(12) United States Patent
Hoess et al.

(10) Patent No.: US 6,384,188 B1
(45) Date of Patent: *May 7, 2002

(54) LIPOPOLYSACCHARIDE-BINDING AND NEUTRALIZING PEPTIDES

(75) Inventors: Adolf Hoess, Warngau (DE); Robert C. Liddington, Boston, MA (US); George R. Siber, Irvington, NY (US)

(73) Assignee: Dana-Farber Cancer Institute, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/477,778

(22) Filed: Jun. 7, 1995

Related U.S. Application Data

(60) Division of application No. 08/416,880, filed as application No. PCT/EP94/02747 on Aug. 18, 1994, now abandoned, which is a continuation-in-part of application No. 08/111,625, filed on Aug. 25, 1993, now abandoned, which is a continuation-in-part of application No. 08/108,415, filed on Aug. 18, 1993, now abandoned.

(51) Int. Cl.$^7$ ............................................. C07K 17/00
(52) U.S. Cl. ...................... 530/326; 530/327; 530/328; 530/811; 530/812; 530/814; 530/815; 530/817; 514/2; 514/13
(58) Field of Search ................................ 530/328, 811, 530/812, 814, 815, 817, 326, 327; 514/2, 13

(56) References Cited

U.S. PATENT DOCUMENTS

| | | | |
|---|---|---|---|
| 5,245,013 A | | 9/1993 | Ulevitch et al. ............. 530/380 |
| 5,594,113 A | * | 1/1997 | Wainwright et al. ......... 530/395 |
| 5,652,211 A | * | 7/1997 | Porro ........................... 514/11 |
| 5,652,332 A | * | 7/1997 | Little, II ...................... 530/324 |

FOREIGN PATENT DOCUMENTS

| | | |
|---|---|---|
| WO | WO 86/06279 | 11/1986 |
| WO | WO 89/01486 | 2/1989 |
| WO | WO 89/01492 | 2/1989 |
| WO | 8912644 | * 12/1989 |
| WO | WO 92 03535 | 3/1992 |
| WO | 9220715 | * 5/1992 |
| WO | WO 93/1411 | 7/1993 |
| WO | WO 94/20532 | 9/1994 |

OTHER PUBLICATIONS

J. Aketagawa et al., "Primary Struture of Limulus Anticoagulant Anti–lipopolysaccharide Factor", *J. Biol. Chem.*, 261, pp. 7357–7365 (1986).

J.D. Baumgartner et al., "Association Between Protective Efficacy of Anti–Lipopolysaccharide (LPS) Antibodies and Suppression of LPS–Induced Tumor Necrosis Factor α and Interleukin 6", *J. Exp. Med.*, 171, pp. 889–896 (1990).

J. Bowie et al., "Deciphering the Message in Protein Sequences: Tolerance to Amino Acid Substitutions," *Science*, 247, pp. 1306–1310. (1990).

C. Couturier et al., "Binding Sites for Endotoxins (Lipopolysaccharides) on Human Monocytes", *J. Immun.*, 147, pp. 1899–1904 (1991).

W.A. Craig et al., "Prevention of the Generalized Shwartzman Reaction and Endotoxin Lethality by Polymyxin B Localized in Tissues", *Infect. Immun.*, 10, pp. 287–292 (1974).

R.J. Duma, "Gram–Negative Bacillary Infections. Pathogenic and Pathophysiologic Correlates", *Am. J. Med.*, 78, pp. 154–163 (1985).

C. Galanos et al., "Synthetic and Natural *Escherichia coli* Free Lipid A Express Identical Endotoxic Activities", *Eur. J. Biochem.*, 148, pp. 1–5 (1985).

H. Gazzano–Santoro et al., "Competition between rBPI$_{23}$, a Recombinant Fragment of Bactericidal/Permeability–Increasing protein, and Lipopolysaccharide (LPS)–Binding Protein for Binding to LPS and Gram–Negative Bacteria", *Infection and Immunity* 62, pp. 1185–1191. (1994).

M.P. Glauser et al., "Septic Shock: Pathogenesis", *Lancet*, 338, pp. 732–736 (1991).

B. Gray et al., "Bactericidal Activity of Synthetic Peptides Based on the Structure of the 55–kilodalton Bactericidal protein from Human Neutrophils," *Infection and Immunity*, 62, pp. 2732–2739. (1994).

A. Hoess et al., "Crystal Structure of an Endotoxin Neutralizing Protein from the Horseshoe Crab, Limulus anti LPS Factor, at 1.5 A Resolution", *EMBO J* 12, pp. 3351–3356. (1993).

S.D.H. Kent, "Chemical Synthesis of Peptides and Proteins", *Ann. Rev. Biochem.*, 57, pp. 957–989 (1988).

M.N. Marra et al., "The Role of Bactericidal/Permeability––Increasing Protein as a Natural Inhibitor of Bacterial Endotoxin", *J. Immun.*, 148, pp. 532–537 (1992).

(List continued on next page.)

Primary Examiner—Dwayne C. Jones
Assistant Examiner—C. Delacroix-Muirheid
(74) Attorney, Agent, or Firm—Fish & Neave; James F. Haley, Jr.; Scott D. Miller

(57) ABSTRACT

Substance which bind with high affinity to endotoxin (lipopolysaccharide [LPS]), and which are useful for the prevention or treatment of, for example, Gram-negative and Gram-positive bacterial sepsis, and for the treatment of bacterial and fungal infections as well as for neutralizing effects associated with heparin. The substances are LPS-binding peptides comprising an LPS-binding domain. DNA sequences encoding peptides, recombinant microorganisms containing the DNA, pharmaceutical compositions containing the peptides of the invention, and diagnostic kits. Methods for the detection and removal of bacterial LPS from solutions.

16 Claims, 20 Drawing Sheets

OTHER PUBLICATIONS

K. Meszaros et al., "Monocyte Tissue Factor Induction by Lipopolysaccharide (LPS): Dependence on LPS–Binding Protein and CD14, and Inhibition by a Recombinant Fragment of Bactericidal/Permeability–Increasing Protein", *Blood* 83, pp. 2516–2525. (1994).

D.C. Morrison et al., "Binding of Polymyxin B to the Lipid A Portion of Bacterial Lipopolysaccharides", *Immunochem.*, 13, 813–18 (1976).

T. Muta et al., "Primary Structure of Anti–Lipopolysaccharide Factor from American Horseshoe Crab, Limulus Polyphemus", *J. Biochem.*, 101, pp. 1321–1330 (1987).

M. Porro, "Structural Basis of Endotoxin Recognition by Natural Polypeptides", *Trends in Microbiology* 2, pp. 65–67. (1994).

C.R.H. Raetz, "Biochemistry of Endotoxins", *Annu. Rev. Biochem.*, 59, pp. 129–170 (1990).

A. Rustici et al., "Molecular Mapping and Detoxification of the Lipid A Binding Site by Synthetic Peptides", *Science*, 259, pp. 361–365 (1993).

R.R. Schumann et al., "Lipopolysaccharide Binding Protein: Its Role and Therapeutical Potential in Inflammation and Sepsis," *Biochem. Soc. Transactions*, 22, pp. 80–82 (1993).

R.R. Schumann et al., "Structure and Function of Lipopolysaccharide Binding Protein", *Science*, 249, pp. 1429–1431 (1990).

T. Shieh et al., "Synthesis and Properties of Tachyplesin I, 9 Lipopolysaccharide–binding Pepide from *Tachypleus tridentatus,*" *FEBS LETT.* 22, pp. 121–124. (1989).

P. Tobias, "A Family of Lipopolysaccharide Binding Proteins Involved in Response to Gram–negative Sepsis," *J. Biol. Chem.*, 263, pp. 13479–13481 (1988).

M. Velucchi et al., "Molecular Requirements of Peptide Structures Binding to the Lipid–A Region of Bacterial Endotoxins," *Vaccines '94*, pp. 141–146 (1994).

H.S. Warren et al., "Binding and Neutralization of Endotoxin by Limulus Antilipopolysaccharide Factor", *Infect. Immun.*, 60, pp. 2506–2513 (1992).

S.D. Wright et al., "Septin: A Factor in Plasma that Opsonizes Lipopolysaccharide–Bearing Particles for Recognition by CD14 on Phagocytes", *J. Exp. Med.*, 176, pp. 719–727 (1992).

E.J. Ziegler et al., "Treatment of Gram–Negative Bacteremia and Shock with Human Antiserum to a Mutant *Escherichia coli*", *N. Eng. J. Med.*, 307, pp. 1225–1230 (1982).

E.J. Ziegler et al., "Treatment of Gram–Negative Bacteremia and Septic Shock with HA–1A Human Monoclonal Antibody Against Endotoxin", *N. Eng. J. Med.*, 324, pp. 429–436 (1991).

H CAPLUS AN 1991: 24608, Cuervo et al., w0 9006 129, (abstract), 1990.*

* cited by examiner

SCHEMATIC DRAWING OF THE LALF-LOOP WITH THE
ALIGNED SEQUENCES OF LBP AND BPI.

LSR  RKK
KFF  RRQ
WFL  FVA
KKK  TKK
YLM  PWW
KQS  KRK
GGG  IGG
KSN  RQS
FFF  YVI
50    HRK
      32

*FIG. 1*

SEQUENCE OF THE PEPTIDES COMPRISING DIFFERENT LENGTHS OF THE LALF-LOOP.

(i) AMINO ACIDS 31 - 52; C - H - Y - R - I - K - P - T - F - R - R - L - K - W - K - Y - K - G - K - F - W - C (SEQ ID NO:8)
(ii) AMINO ACIDS 38 - 45; C - T - F - R - R - L - K - W - K - C (SEQ ID NO:9)

FIG. 2

FIG. 3 SEQUENCE OF THE PEPTIDES TO DETERMINE THE MINIMAL LPS BINDING DOMAIN IN LBP.

(i) AMINO ACIDS 90 - 101; C - R - W - K - V - R - K - S - F - F - K - Q - C (SEQ ID NO:10)
(ii) AMINO ACIDS 90 - 97; C - R - W - K - V - R - K - S - F - C (SEQ ID NO:11)
(iii) AMINO ACIDS 92 - 99; C - K - V - R - K - S - F - F - K - C (SEQ ID NO:12)

FIG. 4 SEQUENCE OF THE PEPTIDES TO DEFINE THE MINIMAL LPS BINDING DOMAIN IN BPI.

(i) AMINO ACIDS 90 - 101; C - K - W - K - A - Q - K - R - F - L - K - M - S - C (SEQ ID NO:13)
(ii) AMINO ACIDS 90 - 97; C - K - W - K - A - Q - K - R - F - C (SEQ ID NO:14)

FIG. 5

SEQUENCE ALIGNMENT OF LALF RESIDUES 32 TO 50 WITH THE INVERSE SEQUENCE OF LBP AND BPI FROM AMINO ACID 103 TO 85.

| | | | | | | | | | | | | | | | | | | | |
|---|---|---|---|---|---|---|---|---|---|---|---|---|---|---|---|---|---|---|---|
| | 32 | | | | | | | | | | | | | | | | | | 50 |
| LALF: | H | Y | R | I | K | P | T | F | R | R | L | K | W | K | Y | K | G | K | F |
| | 103 | | | | | | | | | | | | | | | | | | 85 |
| LBP: | S | G | Q | L | K | F | F | S | K | R | V | K | W | R | G | Q | V | R | I |
| | 103 | | | | | | 8 | 7 | 6 | 5 | 4 | 3 | 2 | 1 | | | | | 85 |
| BPI: | N | G | S | M | K | L | F | R | K | Q | A | K | W | K | G | S | I | K | I |

SEQUENCE OF THE PEPTIDES IN THE INVERSE ORIENTATION OF THE LALF, LBP AND BPI SEQUENCES.

(i) LALF AMINO ACIDS 45 TO 38; C - K - W - K - L - R - R - F - T - C
(ii) LBP AMINO ACIDS 97 TO 90; C - F - S - K - R - V - K - W - R - C
(iii) BPI AMINO ACIDS 97 TO 90; C - F - R - K - Q - A - K - W - K - C SEQUENCE OF THE PEPTIDES IN WHICH POINT MUTATIONS (UNDERLINED) ARE INTRODUCED IN THE LPS-BINDING PEPTIDES DERIVED FROM LBP.

(i) MUTATED LBP AMINO ACIDS 90 TO 97; C - S - E - K - R - V - K - W - K - C
(ii) MUTATED INVERTED LBP AMINO ACIDS 90 TO 97; C - K - W - K - V - R - K - E - S - C

FIG. 7

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Thr Phe Arg Arg Leu Lys Trp Lys
1               5

(2) INFORMATION FOR SEQ ID NO: 2:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

Arg Trp Lys Val Arg Lys Ser Phe Phe Lys Leu Gln
1               5                   10

(2) INFORMATION FOR SEQ ID NO: 3:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 3:

Lys Trp Lys Ala Gln Lys Arg Phe Leu Lys Met Ser
1               5                   10

(2) INFORMATION FOR SEQ ID NO: 4:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1
            (D) OTHER INFORMATION: /note= "Xaa at position 1 is
                beta-alanine."

(xi) SEQUENCE DESCRIPTION: SEQ ID NO: 4:

Xaa Lys Cys Phe Thr Arg Arg Ala Lys Trp Arg Cys
1               5                   10

(2) INFORMATION FOR SEQ ID NO: 5:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1
            (D) OTHER INFORMATION: /note= "Xaa at position 1 is
                beta-alanine."

(xi) SEQUENCE DESCRIPTION: SEQ ID NO: 5:

Xaa Cys Lys Trp Lys Ile Arg Lys Phe Ser Cys Asn
1               5                   10

(2) INFORMATION FOR SEQ ID NO: 6:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 6:

Gly Ala Thr Pro Glu Asp Leu Asn Thr Leu
1               5                   10

(2) INFORMATION FOR SEQ ID NO: 7:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 7:

Ile Lys Thr Lys Lys Phe Leu Lys Lys Thr
1               5                   10

(2) INFORMATION FOR SEQ ID NO: 8:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Cys His Tyr Arg Ile Lys Pro Thr Phe Arg Arg Leu Lys Trp Lys Tyr
1               5                   10                  15
Lys Gly Lys Phe Trp Cys
            20

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Cys Thr Phe Arg Arg Leu Lys Trp Lys Cys
1               5                   10

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Cys Arg Trp Lys Val Arg Lys Ser Phe Phe Lys Leu Gln Cys
1               5                   10

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Cys Arg Trp Lys Val Arg Lys Ser Phe Cys
1               5                   10

(2) INFORMATION FOR SEQ ID NO: 12:

(i) SEQUENCE CHARACTERISTICS:
        (A) LENGTH: 14 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 12:

```
Cys Lys Trp Lys Ala Gln Lys Arg Phe Leu Lys Met Ser Cys
1               5                  10
```

(2) INFORMATION FOR SEQ ID NO: 13:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Cys Lys Trp Lys Ala Gln Lys Arg Phe Cys
1               5                  10
```

(2) INFORMATION FOR SEQ ID NO: 14:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Cys Lys Val Arg Lys Ser Phe Phe Lys Cys
1               5                  10
```

(2) INFORMATION FOR SEQ ID NO: 15:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
His Tyr Arg Ile Lys Pro Thr Phe Arg Arg Leu Lys Trp Lys Tyr Lys
1               5                  10                 15
Gly Lys Phe
```

(2) INFORMATION FOR SEQ ID NO: 16:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

```
Ser Gly Gln Leu Lys Phe Phe Ser Lys Arg Val Lys Trp Arg Gly Gln
1               5                  10                 15
Val Arg Ile
```

(2) INFORMATION FOR SEQ ID NO: 17:

(i) SEQUENCE CHARACTERISTICS:
    (A) LENGTH: 19 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 17:

```
Asn Gly Ser Met Lys Leu Phe Arg Lys Gln Ala Lys Trp Lys Gly Ser
1               5                   10                  15
Ile Lys Ile
```

(2) INFORMATION FOR SEQ ID NO: 18:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

```
Cys Lys Trp Lys Leu Arg Arg Phe Thr Cys
1               5                   10
```

(2) INFORMATION FOR SEQ ID NO: 19:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

```
Cys Phe Ser Lys Arg Val Lys Trp Arg Cys
1               5                   10
```

(2) INFORMATION FOR SEQ ID NO: 20:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

```
Cys Phe Arg Lys Gln Ala Lys Trp Lys Cys
1               5                   10
```

(2) INFORMATION FOR SEQ ID NO: 21:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

```
Cys Ser Phe Lys Arg Val Lys Trp Lys Cys
1               5                   10
```

(2) INFORMATION FOR SEQ ID NO: 22:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

```
Cys Lys Trp Lys Val Arg Lys Phe Ser Cys
1               5                   10
```

LIPOPOLYSACCHARIDE-BINDING AND NEUTRALIZING PEPTIDES

This is a divisional of prior U.S. application Ser. No. 08/416,880 filed on May 30, 1995, (now abandoned), which is a 371 of PCT/EP94/02747, filed Aug. 18, 1994, which is a continuation-in-part of Ser. No. 08/111,625 filed Aug. 25, 1993 now abandoned which is a continuation in part of Ser. No 08/108,415, filed Aug. 18, 1993, abandoned.

The present invention relates to substances which bind with high affinity to endotoxin (lipopolysaccharide [LPS]), and which are useful for the prevention or treatment of a variety of conditions and diseases, such as of Gram-negative and Gram-positive bacterial sepsis, or bacterial or fungal infections. Furthermore, said substances may be used for neutralizing effects associated with heparin. The substances are LPS-binding peptides comprising an LPS-binding domain. The invention also encompasses methods for the detection and removal of bacteria LPS from solutions.

In humans, LPS released during infection by Gram-negative bacteria can cause the severe pathological changes associated with septic shock (Duma, *Am. J. Med.* 78 (1985) 154–163; Glauser et al., *Lancet* 338 (1991), 732–736). In the United States, septic shock is responsible for between 100,000 and 300,000 deaths annually (Ziegler et al., *N. Eng. J. Med.* 324 (1991), 429–436) and in Germany for between 70,000 and 100,000. Although a variety of agents have been evaluated for neutralizing LPS or enhancing its clearance in vivo, there remains no specific treatment for Gram-negative bacterial sepsis.

LPS is a glycolipid that is ubiquitous in the outer membrane of Gram-negative bacteria (Raetz, *Annu. Rev. Biochem.* 59 (1990), 129–170). LPS consists of an oligosaccharide and a lipid portion and is characterized by an overall negative charge, stability to heat, and high molecular weight. While the chemical structure of most LPS molecules is complex and diverse, a common feature is the lipid A region. Lipid A, the membrane anchor of LPS, consists of a central phosphodisaccharide unit that is attached to up to seven fatty acid chains. Most of the biological activities of LPS reside in the lipid A portion (Galanos et al., *Eur. J. Biochem.* 145, (1985), 1–5).

Septic shock is complex condition which arises from a cascade of molecular and cellular events following infection by microorganisms, predominant among which are Gram-negative bacteria. The onset of shock arises from the interaction of LPS or lipid A with membrane-bound receptors on macrophages and blood monocytes (Couturier et al., *J. Immun.* 147 (1991), 1899–1904) or various serum proteins, such as the septins (Wright et al., *J. Exp. Med.* 176 (1992), 719–727). These interactions lead to an increase in the levels of pro-inflammatory mediators such as tumor necrosis factor, IL-1, IL-6, and interferon-c. Endothelial cells are also stimulated to produce factors which attract neutrophils. Release of enzymes and other factors by activated neutrophils causes damage to local vasculature which can lead rapidly to death.

One approach to the treatment of sepsis is the use of substances which bind to LPS and neutralize its toxic effects in vivo. Although there are numerous proteins which bind LPS, the number of substances which effectively neutralize LPS in vivo are very few. A number of such substances have been identified, including polymyxins (Morrison et al., *Immunochem.* 13 (1976), 813–818), polymyxin-derived peptides (Rustici et al., *Science* 259 (1993), 361–365), polyclonal (Ziegler et al., *N. Eng. J. Med.* 307 (1982), 1225–1230) and monoclonal (Ziegler et al. (1991), loc. cit.) antibodies, bactericidal/permeability-increasing protein (BPI) (Marra et al., *J. Immun.* 148 (1992), 532–537), lipopolysaccharide binding protein (LBP) (Schuhmann et al., *Science* 249 (1990), 1429–1431), and Limulus anti-LPS factor (LALF) (Akategawa et al., *J. Biol. Chem.* 261 (1986), 7357–7365, Muta et al., *J. Biochem.* 101 (1987), 1321–1330).

The simplest molecules that bind to the lipid A portion of LPS with high affinity are the polymyxin antibiotics; these are positively charged amphipathic cyclic oligopeptides attached to a lipid tail. Although polymyxins bind to LPS/ lipid A with high affinity, they suffer the drawback from a therapeutic stand-point of having unacceptably high toxicity (Craig et al., *Infect. Immun.* 10 (1974), 287–292). The LPS-binding monoclonal antibodies HA-1A and E5 both failed to demonstrate positive clinical effects for the treatment of Gram-negative septic shock. One of the main problems associated with these antibodies is non-specificity; for example, HA-1A binds tightly to numerous hydrophobic structures apart from lipid A (see, for example, Baumgartner et al., *J. Exp. Med.* 171 (1990), 889–896). The human proteins BPI and LBP are both being investigated for the treatment of Gram-negative sepsis (Marra et al., loc. cit.; Ulevitch et al. (1986), WP 86/06279). BPI, which s stored in specific granules of polymorphonuclear cells, kills Gram-negative bacteria by binding to membrane-bound LPS and disrupting the permeability barrier. LBP is a mammalian serum protein which also binds very tightly to LPS. Although LBP shares sequence homology with BPI (Schuhmann et al., loc. cit.), it is not directly cytotoxic to Gram-negative bacteria and its precise function is obscure. Most recently, LALF has been investigated for use in sepsis (Warren et al., *Infect. Immun.* 60 (1992), 2506–2513; Wainwright et al. (1992) WO 92/20715). This protein is almost certain to suffer the disadvantages associated with other foreign proteins for human therapy; it is immunogenic and has only a short half-life in circulation. These factors will reduce its clinical potential. None of these substances have been proven to be effective for the treatment of the serious conditions associated with Gram-negative infection.

Thus, the technical problem underlying the present invention is to provide substances which bind LPS released by Gram-negative bacteria, neutralize its toxic effects, and exhibit no toxicity.

The solution to the above technical problem was achieved by providing substances which relate to peptides which bind tightly to LPS, and therefore have utility in the diagnosis and treatment of Gram-negative and other septic conditions.

Thus, the present invention relates to LPS-binding peptides comprising an LPS-binding domain comprising at least:

(a) the amino acid sequence 1-2-3-4-5-6-7-8, wherein the numbers represent any of the following amino acids:
  1=a polar or positively charged amino acid, preferably C, H, K, N, Q, R, S, T, W, or Y;
  2=a hydrophobic amino acid, preferably A, F, H, I, L, M, V, or W;
  3=a basic amino acid, preferably H, K, or R;
  4=a hydrophobic or positively charged amino acid, preferably A, F, H, I, K, L, M, R, V, or W;
  5=a hydrophobic, polar, or positively charged amino acid, preferably A, C, F, H, I, K, L, M, N, Q, R, S, T, V, W, or Y;
  6=a positively charged amino acid, preferably K or R;
  7=A hydrophobic, polar, or positively charged amino acid, preferably A, C, F, H, I, K, L, M, N, Q, R, S, T, V, W, or Y;

8=a hydrophobic or positively charged amino acid, preferably A, F, H, I, K, L, M, R, V, or W;

(b) a corresponding inverse amino acid sequence; or (c) a variation of said amino acid sequence (a) or (b) capable of effectively binding to LPS.

The peptides of the present invention effectively bind to LPS, i.e. they interact specifically with LPS with an association constant greater than $10^5$ $M^{-1}$. In this context, an LPS-binding peptide is a chain of amino acids linked to each other by peptide bonds. An LPS-binding domain is the shortest possible chain of amino acids within an LPS-binding peptide which effectively binds to LPS.

All peptide structures disclosed use the single letter code for amino acids.

DESCRIPTION OF FIGURES

FIG. 1: A schematic diagram of the LALF loop indicating the direction of side-chains and the putative locations of the corresponding residues in LBP and BPI. The three letters at each position correspond to the amino acid residues in LALF, LBP and BPI, respectively. Solid bonds/dashed bonds indicate side chains pointing out of/into the plane of the diagram.

FIG. 2 shows the peptides which are used to define a minimum LPS-binding domain in LALF. The two cysteine residues are linked by a disulphide bond.

FIG. 3 shows the peptides which are used to define a minimum LPS-binding domain in LBP. The two cysteine residues are linked by a disulphide bond.

FIG. 4 shows the peptides which are used to define the LPS-binding domain in BPI. The two cysteine residues are linked by a disulphide bond.

FIG. 5 shows the aligned sequences of LALF, LBP and BPI in which the LBP and the BPI sequences are listed from the C-terminus to the N-terminus while the LALF sequence is written from the N-terminus to the C-terminus.

FIG. 6 shows the peptides which are used to define the LPS-binding activity in the inverse orientation. The two cysteine residues are linked by a disulphide bond.

FIG. 7 shows a list of the peptides in which point mutations are introduced into peptides resembling the minimal LPS binding domain of LBP. The two cysteine residues are linked by a disulphide bond.

Figure 8:
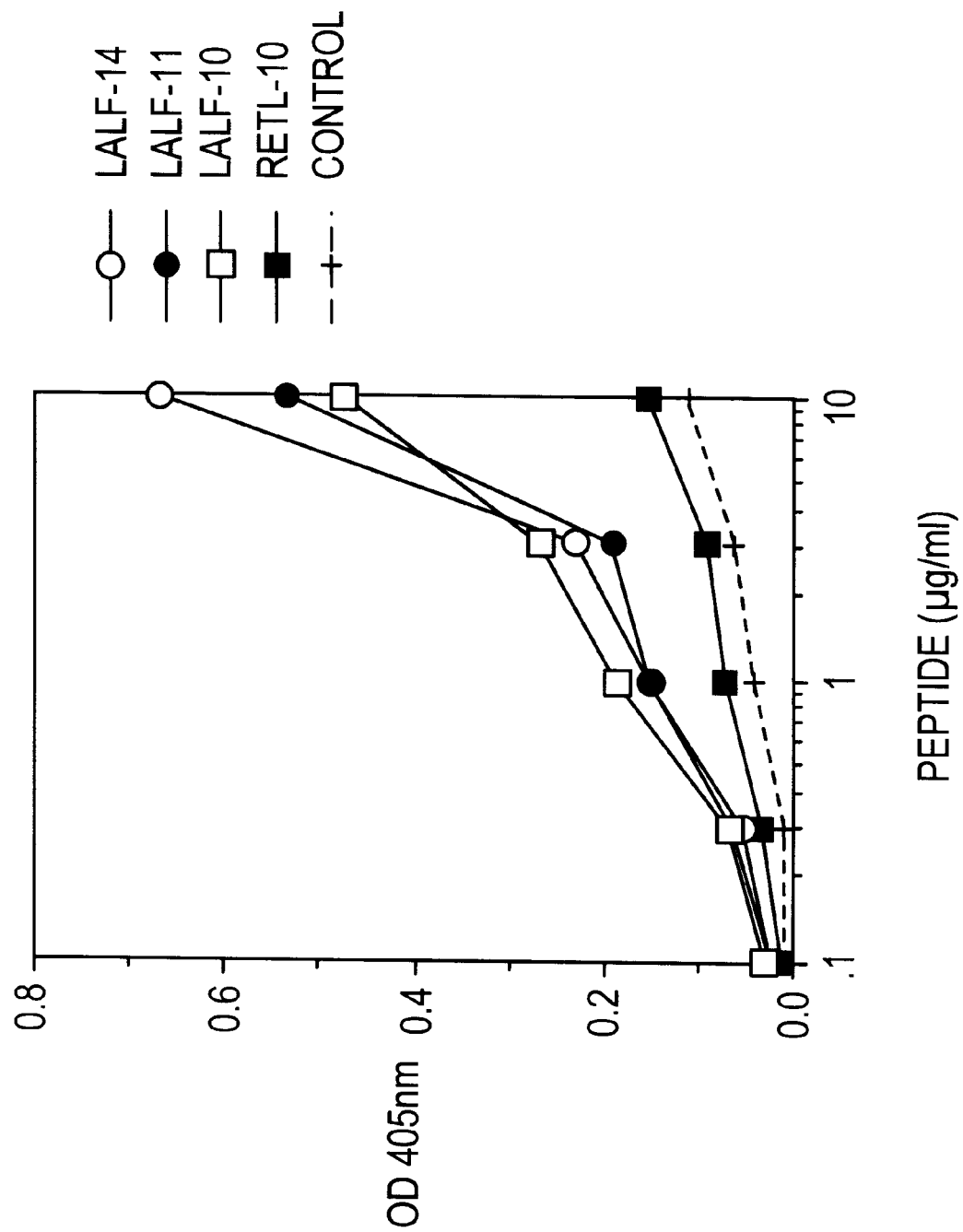
FIG. 8 shows ELISA data for the binding of LALF-derived peptides to lipid A. The four biotinylated peptides are allowed to bind to immobilized lipid A, and bound peptide is detected using a streptavidin-alkaline phosphatase conjugate. For more details, see Example 1.

It has surprisingly been found by the inventors that the crystal structure of LALF reveals a novel but simple tertiary fold which has a striking shape and amphipathicity. A surface-extended loop in the LALF structure (loop of LALF or LALF-loop) has similar features to polymyxin B by being positively charged and amphipathic and having several exposed hydrophobic and aromatic residues. Furthermore, the loop of LALF is distinguished by an alternating series of positively charged and hydrophobic/aromatic residues that, by virtue of the extended β-conformation, point in opposite directions, and a single pair of positive charges, that, because of the β-turn conformation, point in the same direction and maintain the amphipathicity. The loop contains no negatively charged amino acids. A similar amphipathic loop exists in three other proteins which bind LPS: rabbit and human lipopolysaccharide-binding protein (LBP) and human bactericidal/permeability-increasing protein (BPI) (FIG. 1). Inspection of the LBP and BPI sequences reveals a similar pattern of alternating residues that could produce an amphipathic loop; the 19 residue stretch contains six basic and no acidic amino acids. Near the top of the loop, one amphipathic pair of residues (Ser/Arg96 and Phe97) is reversed, but it is possible that a different conformation of the hairpin turn would maintain the amphipathicity of the loop in BPI and LBP. The deduced sequence and structural homology within this set of LPS-binding proteins led to the design of the peptides which are the subject of the present invention. All of the LPS-binding peptides encompassed by the present invention can be prepared using standard methods of peptide synthesis, as described by, for example, S. D. H. Kent (Ann. Rev. Biochem. 57, (1988), 957), which is apparent to anyone skilled in the art. Alternatively, the peptides can be synthesized biologically using a recombinant microorganism which has been genetically engineered to contain DNA sequences encoding the peptides (Sambrook et al., *Molecular Cloning, A Laboratory Manual,* CSH Press (1989)).

In another embodiment, the present invention relates to peptides having an inverse amino acid sequence derived from an LPS-binding peptide and also effectively binding to LPS. Thus, the present invention also encompasses such peptides. In this context, an inverse amino acid sequence is a chain of amino acids which, when read from the N-terminus to the C-terminus, has the same sequence as the parent peptide when read from the C-terminus to the N-terminus. There exists homology between LBP/BPI sequences from amino acids 90 to 97 and the LALF sequence from residues 38 to 45 when the LBP/BPI sequence is read from the C-terminus to the N-terminus (FIG. 5). On this basis, "inverse" peptides were synthesized and tested for their ability to bind LPS. Particularly preferred are the inverse peptides shown in FIG. 6 which effectively bind to LPS, as shown by ELISA.

In still another embodiment, the present invention relates to peptides which share a common structural motif with the above peptides and are also able to bind LPS. Thus, the present invention also provides for an LPS-binding peptide comprising an LPS-binding domain in which the amino acid sequence includes a variation. In this context, a variation of an amino acid sequence refers to any changes in the sequence that are introduced either by an insertion or a deletion of one or more amino acids. Particularly preferred are the peptides shown in FIG. 7, in which mutations have been introduced in the parent peptide structure. These altered peptides both bind to LPS, as shown by ELISA.

In a preferred embodiment, the present invention provides LPS-binding peptides, wherein the amino acid sequence (a) is any combination of the amino acids seen in the LPS-binding loops of LALF, LBP, or BPI, namely:

1=T or R or K
2=F or W
3=R or K
4=R or V or A
5=L or R or Q
6=K
7=W or S or R
8=K or F

In further preferred embodiment, the present invention provides peptides of the general motif outlined above, with the additional feature that the N-terminus is extended by two or more amino acids denoted −2 and −1, in which amino acid −2 which is the new N-terminus, is taken from the set R, K, H, N and Q, and amino acid −1 is any amino acid.

In a further preferred embodiment, the present invention provides peptides of the general motif outlined above with the additional feature that the C-terminus is extended by addition of cysteine, and the N-terminus is extended by two or more amino acids denoted −2 and −1 in which the amino acid −2, which is the new N-terminus, is taken from the set R, K, H, N and Q, and amino acid −1 is cysteine, the two cysteines being linked by a disulphide bond.

In a more preferred embodiment, the LPS-binding peptides have the amino acid sequence TFRRLKWK(SEQ ID NO:1), RWKVRKSFFKLQ(SEQ ID NO:2), or KWKAQKRFLKMS(SEQ ID NO:3).

In a further preferred embodiment, the present invention provides linear peptides which are able to bind LPS effectively. Particularly preferred are peptides derived from LALF. Disulfide-constrained circular peptides (see below) spanning amino acids 31 to 52 and amino acids 38 to 45 of LALF are incubated with DTT to reduce the disulfide bond. The peptide spanning amino acids 31 to 52 binds effectively to lipid A as determined by ELISA. The peptide spanning residues 38 to 45 interacts only weakly with lipid A, as determined by ELISA.

In a still further preferred embodiment, the present invention provides for peptides which effectively bind to LPS and are constrained to adopt a circular conformation by an intramolecular bridge. In this context, the circular conformation can be brought about by any one of a number of intramolecular bridges. Preferably, the peptide may incorporate two cysteine residues between which a disulfide bond is formed by an oxidation reaction. Alternatively, the two cysteines may be linked through a homo-bifunctional cross-linking reagent, such as a bis-maleimide. Particularly preferred are the cyclic peptides comprising amino acids 31 to 52 and amino acids 38 to 45 of LALF, each stabilized by a disulfide bond formed between two cysteine residues, producing a cyclic conformation (FIG. 2). Both bind lipid A and, additionally, two different types of LPS-molecules, *E. coli* J5-LPS and *E. coli* EH 100 LPS, as determined by ELISA. This defines a minimal LPS-binding domain to be the peptide spanning amino acids 38 to 45 of LALF. Peptides derived from LBP according to the alignment as shown in FIG. 1, which are constrained to adopt a cyclic conformation by means of a disulfide bond formed between two unique cysteine residues, are also able to bind LPS, as shown by ELISA. Thus, particularly preferred are also the peptides spanning amino acids 90 to 101 and amino acids 90 to 97 of LBP (FIG. 3). Conversely, the peptide spanning amino acids 92 to 99 of LBP does not bind LPS. This defines a second minimal LPS binding domain to be the peptide spanning amino acids 90 to 97 of LBP. Furthermore, the fact that the peptide ranging from amino acids 92 to 99 does not bind lipid A although it is positively charged and amphipathic indicates that these features alone are not sufficient to provide an LPS-binding motif, further illustrating the novelty of the present invention. Peptides derived from BPI according to the alignment shown in FIG. 1, which are constrained to adopt a cyclic conformation by means of a disulfide bond between two unique cysteine residues, are also able to bind LPS as shown by ELISA. Particularly preferred are the peptides spanning amino acids 90 to 97 and amino acids 90 to 101 of BPI (FIG. 4). This defines a third minimal LPS-binding domain to be the peptide spanning amino acids 90 to 97 of BPI.

In a further preferred embodiment, the present invention provides a detectably-labeled peptide which can be used in an assay for the determination of LPS in a biological sample. In this context, a detectably-labeled peptide is a peptide which is covalently linked to a substance which can readily be detected. Most commonly, the label is an enzyme, fluorescent substance, or radionuclide. By way of example, the peptide may be linked to an enzyme such as β-galactosidase, peroxidase, or alkaline phosphatase, which, in the presence of an appropriate substrate, can lead to the generation of a colored or fluorescent product which is readily detected. Alternatively, the peptide may be linked directly to a fluorescent substrate, such as fluorescein, rhodamine, or auramine for the purposes of detection. Commonly used labelling radionuclides include $^{14}C$, $^{131}I$, $^{3}H$, $^{125}I$, and $^{35}S$. Many variations on labelling configurations can be imagined. For example, the peptide may be linked through an intermediary substance, such as biotin, to another substance, such as streptavidin, which is itself linked to a substance which enables detection according to conventional methods.

In a preferred embodiment, the present invention provides a set of LPS-binding peptides each comprising one or more LPS-binding domains.

The present invention also includes DNA sequences encoding the peptides of the present invention, as well as vectors, such as plasmids, phagemids, and cosmids containing these DNA sequences.

Additionally, the present invention encompasses microorganisms such as viruses, bacteria and yeast which have been transformed with these vectors. The DNA sequences provided herein are most readily obtained using standard methods of automated DNA synthesis, but can also be obtained by conventional molecular cloning. For example, those DNA sequences derived from the naturally-occurring proteins LBP, BPI, or LALF can be obtained in a form suitable for cloning by use of the polymerase chain reaction, as will be apparent to anyone skilled in the art (Sambrook et al., loc. cit.).

Furthermore, the present invention relates to a method for the production of an LPS-binding peptide according to the invention, comprising culturing a microorganism transformed with a recombinant vector comprising DNA encoding the peptide of the invention, and recovering said peptide or a fusion protein containing it from the medium.

In a preferred embodiment, the present invention provides a pharmaceutical composition comprising effective amounts of any of the peptides described above in combination with a pharmaceutically acceptable carrier and/or diluent. The pharmaceutical composition can be used for the treatment of a variety of conditions related to the release of LPS, especially Gram-negative sepsis. In this context, the term sepsis refers to the morbid conditions induced by a toxin, the introduction or accumulation of which is most commonly caused by infection or trauma. The initial symptoms of sepsis typically include chills, profuse sweat, irregularly remittent fever, prostration and the like, followed by persistent fever, hypotension leading to shock, neutropenia, leukopenia, disseminated intravascular coagulation, adult respiratory distress syndrome and multiple organ failure.

The peptides which are the subject of the present invention are similar in structure to a number of peptides which derive from BPI, which have been the subject of investigation for their therapeutic properties (see, for example, Little et al., *J. Biol. Chem.* 269 (1994) 1865–1872). In addition to their endotoxin binding and neutralization capabilities by comparison with the BPI-derived peptides, the peptides which are described here may be expected to show bactericidal and heparin binding activity. Accordingly, the present invention furthermore provides pharmaceutical compositions which can be used to kill bacteria (both Gram-negative and Gram-positive) and fungi as well as pharmaceutical compositions which possess the ability to neutralize properties associated with heparin, such as anticoagulation, angiogenesis, and growth factor-induced tumour and endothelial cell proliferation.

In a further preferred embodiment, the present invention also encompasses a diagnostic kit. Such a kit would comprise at least a peptide or a labelled peptide as set out above and would consist additionally of the reagents and materials necessary to carry out a standard competition or sandwich assay. Said diagnostic kit can be used for the determination of LPS or for the diagnosis of septic conditions.

In a still further preferred embodiment, the present invention provides the peptides disclosed herein immobilized on a solid support. Most conveniently, the peptide is covalently linked to a solid support such as cellulose, agarose, polyacrylamide, etc, which is modified so as to bear a reactive functionality such as an imidate, activated ester, activated disulfide, epoxide, etc. The peptide can be linked by any one of a number of methods which are commonly used in protein chemistry. By way of example, an N-terminal or C-terminal cysteine can readily be introduced into the peptide during synthesis. The thiol function of this cysteine residue can be used to link the peptide to a solid support which has been derivatized to bear a maleimide group. The present invention also provides a method of removing LPS from solutions, whereby said solution is passed over the immobilized peptides of the invention. This method is of particular interest in the purification of pharmaceutical preparations, LPS contamination of which is a frequently-occurring problem.

Now that the invention has been generally described, it will be illustrated by the following specific examples, which are provided for the purpose of illustration only and are not intended to limit the scope of the invention.

EXAMPLE 1

Binding of Peptides to Lipid A

Peptides are synthesized using standard Fmoc chemistry on an ABIMED AMS 422 synthesizer. The cleaved peptides are oxidized overnight in DMSO at room temperature, purified on a C-18 reversed phase column with a gradient of acetonitrile/0.1% trifluoroacetic acid, and characterized by mass spectroscopy.

To confirm the hypothesis that the loop sequence of LALF binds lipid A and LPS, peptides comprising parts of the LALF loop are synthesized, ranging in length from 8 to 12 amino acids. The peptides comprising amino acids 36 to 47 (LALF-14), and amino acids 38 to 45 (LALF-10) of LALF, are stabilized by a disulfide bond through the introduction of cysteine residues at the N- and C-termini of the peptides, thus adopting a cyclic conformation. The peptide comprising amino acids 36 to 45 (LALF-11), in which amino acid 37 is replaced by a cysteine is also cyclized following introduction of a second cysteine residue at the C-terminus of the peptide. All peptides are labelled at the N-terminus with biotin.

The lipid A-binding activities of the peptides are shown in an ELISA format as follows. An ELISA plate (NUNC, Polysorp 96U) is coated for 90 minutes at 37° C. with 100 μl lipid A in PBS (0.25-1 μg/ml). All further steps are done at room temperature. After washing and blocking (10 min.) with PBS/0.1% Tween, the solid phase is incubated for 1 hour with 100 μl of increasing amounts (0.1 μg/ml–10 μg/ml) of purified synthetic peptides (dissolved in PBST) labelled at the N-terminus with biotin. After washing with PBS/0.1% Tween, the bound peptides are incubated for 45 min. with 100 μl streptavidin conjugated to alkaline phosphatase (Boehringer Mannheim GmbH; 1:10000 diluted in PBS/0.1% Tween), followed again by washing with PBS/ 0.1% Tween and 100 mM Tris pH 9.5. p-Nitrophenylphosphate (2 mg/ml in 100 mM Tris pH 9.5) is used as a substrate for alkaline phosphatase. The ELISA is read at 405 nm.

Increasing amounts of peptide are added to immobilized lipid A. LALF-14, LALF-11 and LALF-10 bind lipid A with high activity (see FIG. 8). The cyclic peptide comprising the inverted sequence from amino acids 38–45, RETL-10, binds lipid A only slightly above background level, which is set by the control peptide. This result indicates that, although RETL-10 is positively charged and amphipathic, these features alone are not sufficient to provide high affinity LPS-binding, illustrating the novelty of the present invention.

The peptides derived from LSP comprising amino acids 90 to 101 (LBP-14), amino acids 92 to 99 (LBP-10-1) and amino acids 90 to 97 (LBP-10-2), the peptide derived from BPI comprising amino acids 90 to 101 (BPI-14), and two peptides comprising an amino acid sequence randomly chosen from the motif defined herein (MS-21 (Biotin-Z-K-C-F-T-R-R-A-K-W-R-C (Z=β-alanine) (SEQ ID NO:4)), MS-22 (Biotin-Z-C-K-W-K-I-R-K-F-S-C-N (Z=β-alanine)) (SEQ ID NO:5)) are stabilized by formation of a disulfide bond formed by the oxidation of cysteines introduced at the N- and C-termini of the peptides, giving cyclic peptides. Each is labelled at the N-terminus with biotin.

Figure 9:
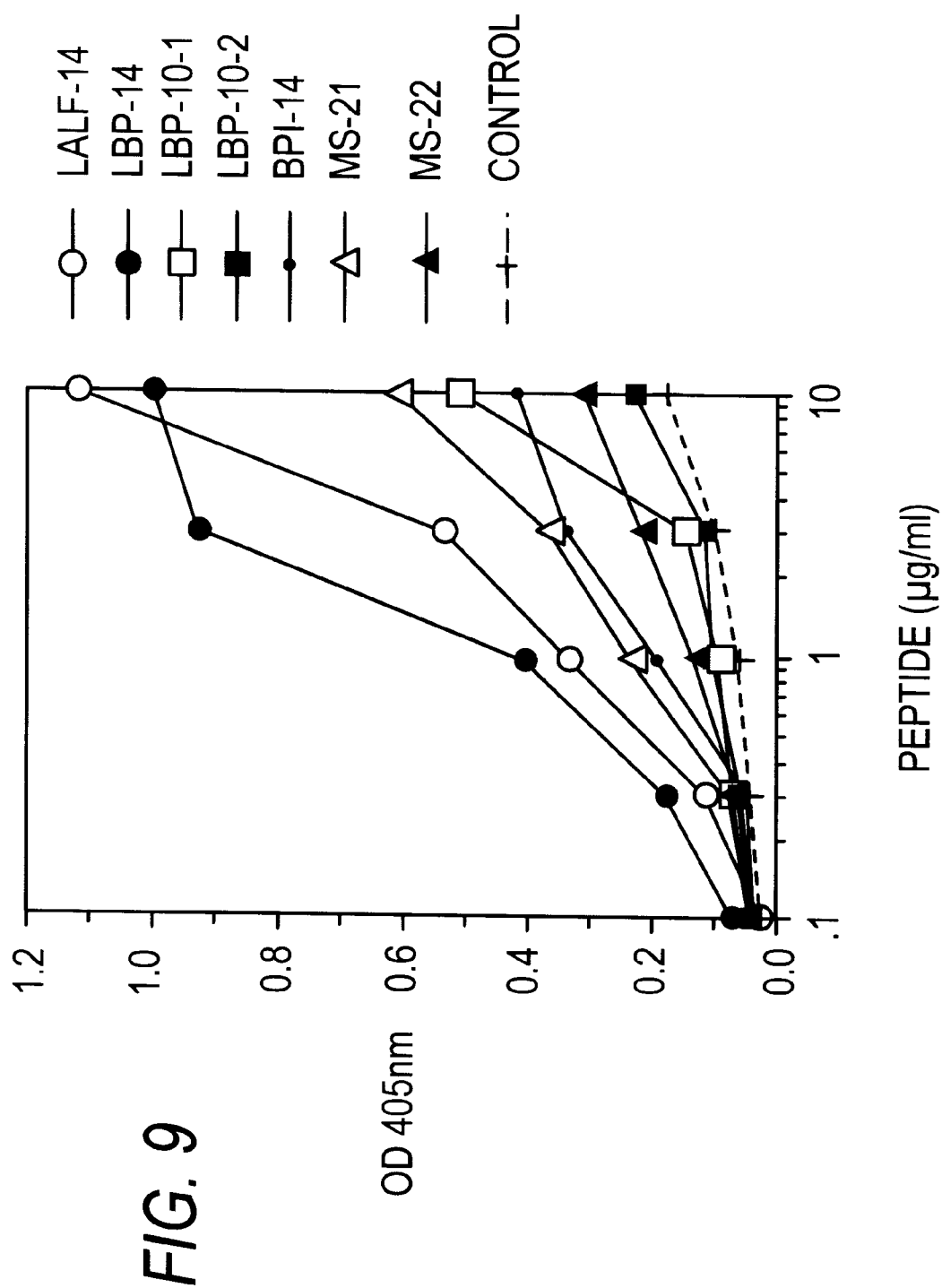
FIG. 9 shows ELISA lipid A binding data for peptides derived from LBP, BPI, and the generalized motif described here in comparison with the LALF-derived peptide. The biotinylazed peptides are allowed to bind to immobilized lipid A, and bound peptide is detected using a streptavidin-alkaline phosphatase conjugate. For more details, see Example 1.

The lipid A-binding activity of the peptides is tested in an ELISA format as described above, in which increasing amounts of peptide is added to immobilized lipid A (see FIG. 9). LALF-14 is used as a control for high activity binding and the irrelevant peptide Nor (G-A-T-P-E-D-L-N-T-L) (SEQ ID NO: 6) to determine background binding. Of the new peptides based on LBP, LBP-14 binds lipid A as well as LALF-14, LBP-10-1 only in its highest concentration (10 μg/ml) binds lipid A above background, while LBP-10-2 binds lipid A only slightly above background. The peptide based on BPI, BPI-14, binds lipid A above background, but significantly weaker than LALF-14 and LSP-14. Of the peptides based on the LPS binding motif, MS-21 and MS-22, MS-21 binds lipid A weaker than LALF-14 and LBP-14, but slightly better than BPI-14. MS-22 binds lipid A clearly above background level and with a similar activity to LBP-10-1, but weaker than MS-21.

EXAMPLE 2

Binding of LALF-14 to Lipid A and LPS

Figure 10:
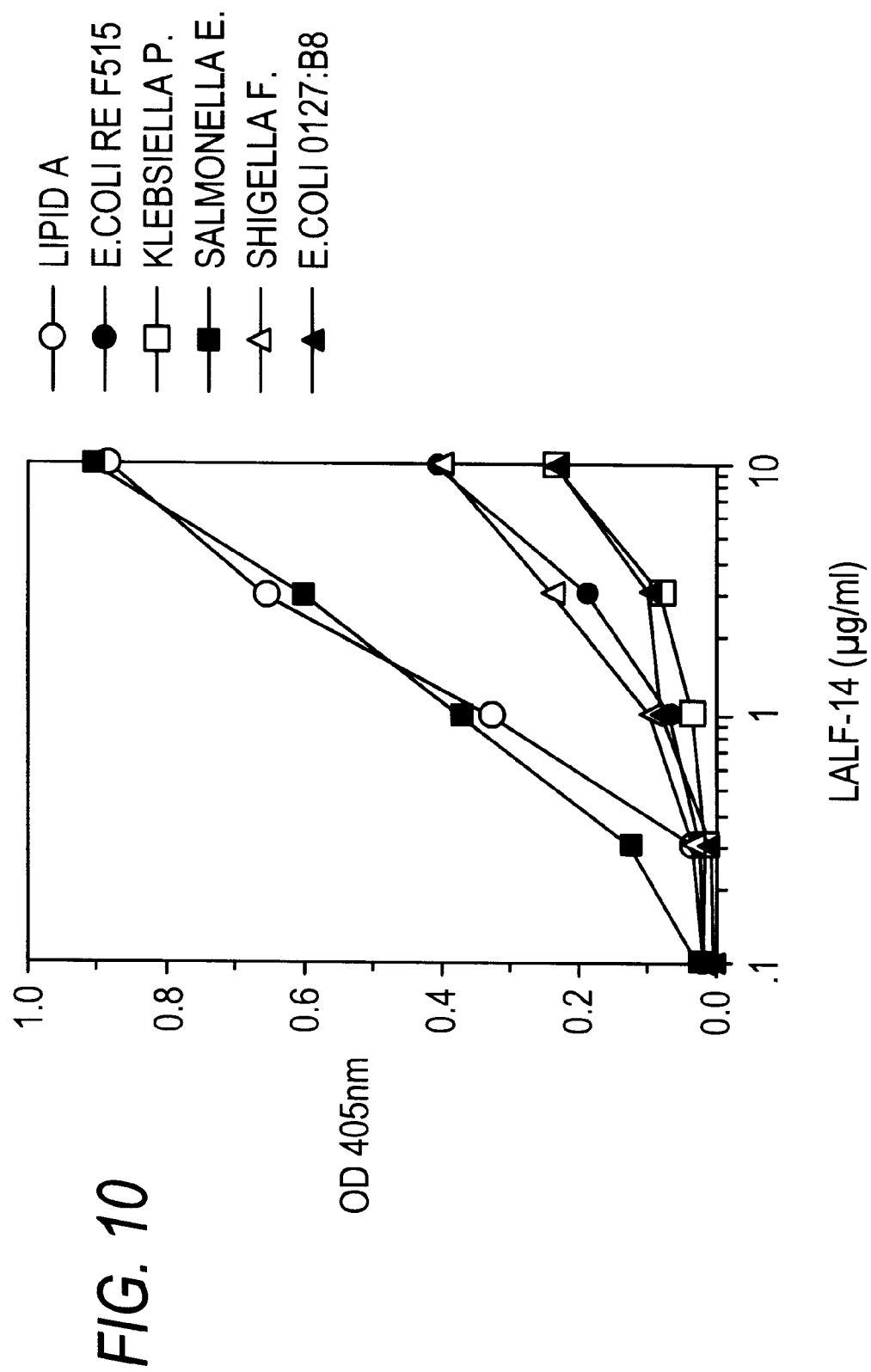
FIG. 10 shows ELISA data for the binding of the LALF-derived peptide LALF-14 to different types of lipopolysaccharide. The biotinylated peptide is allowed to bind to immobilized lipid A or LPS, and bound peptide is detected using a streptavidin-alkaline phosphatase conjugate. For more details, see Example 2.

The cyclic peptide comprising amino acids 36 to 47 of LALF (LALF-14) is tested or binding different kinds of lipopolysaccharides in comparison with lipid A. in an ELISA format in which increasing amounts or peptide are added to immobilized lipid A and LPS. The forms of lipopolysaccharide used are *E. coli* Re F515; Klebsiella p.; Salmonella e.; Shigella f.; and *E. coli* 0127:B8. LALF-14 is able to bind to all species of lipopolysaccharide above background, but with different activities (see FIG. 10). Thus, LALF-14 binds Salmonella e. as well as it binds to lipid A, *E. coli* Re F515 and Shigella f. with less activity than lipid A but with higher activity than Klebsiella p. and *E. coli* 0127:B8.

EXAMPLE 3

Importance of Conformation for Peptide-lipid A Binding

Figure 11:
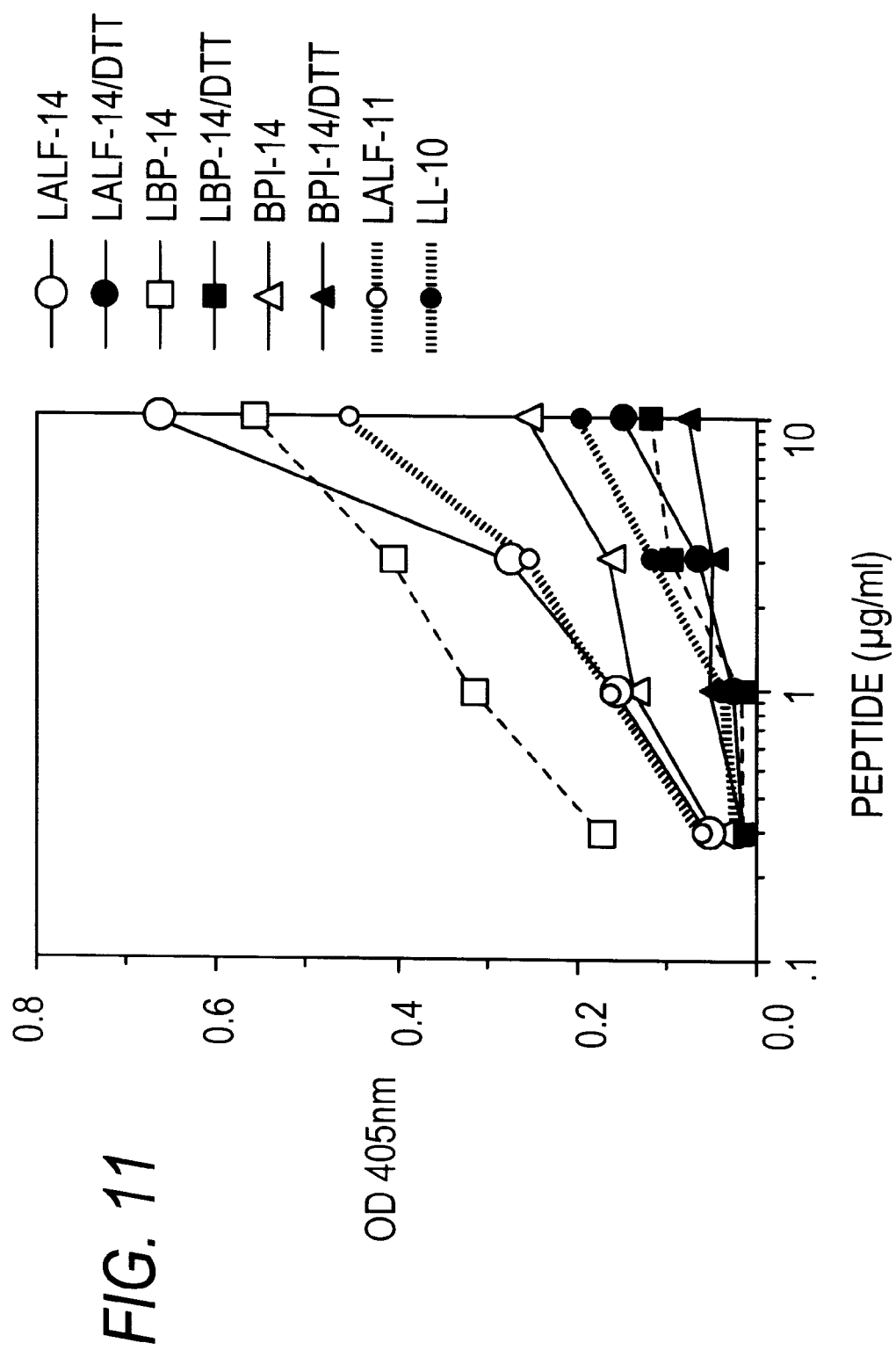
FIG. 11 shows the ELISA data which reveals the difference between cyclic and linear peptides in binding to lipid A. The biotinylated peptides are allowed to bind to immobilized lipid A, and bound peptide is detected using a streptavidin-alkaline phosphatase conjugate. For more details, see Example 3.

To investigate the importance of the constrained conformation for high affinity peptide-lipid A binding, binding activity of cyclic and the corresponding linear peptides is compared. This is achieved (i) by reducing peptides LALF-14, LBP-14 and BPI-14 with DTT to destroy the disulphide bond and (ii) by synthesizing a linear peptide comprising amino acids 36 to 45 (LL-10) for comparison with LALF-11. The lipid A-binding activity of the peptides is tested in an ELISA format (vide infra) in which increasing amounts of peptide are added to immobilized lipid A. In all cases, the oxidized peptides LALF-14, LBP-14 and BPI-14 display higher lipid A binding activity compared with the reduced peptides, LALF-14/DTT, LBP-14 /DTT and BPI-14/DTT, demonstrating that a constrained cyclic form is superior to a linear conformation for high lipid A binding activity (see FIG. 11). This result is confirmed by the observation that the lipid A binding activity of the cyclic peptide LALF-11 is higher than that of its linear counterpart LL-10.

EXAMPLE 4

Binding of Fluorescein-labelled LPS to Biotinylated Peptides

To investigate the potential use of multimeric peptides for increasing the binding to LPS, individual peptides are coated on an ELISA plate to high surface concentrations. Immobilization is performed by first coating the plate with strepravidin and then binding the peptides via their N-terminal biotin groups. Thus, 100 μl streptavidin (Boehringer Mannheim GmbH; 10 μg/ml in PBS) is used for coating followed by washing, blocking (10 min.) with PBS/0.1% Tween and a 30 min. incubation with 100 μl of purified synthetic peptides (1 μg/ml or 10 μg/ml in PBST) labelled at the N-terminus with biotin. After washing with PBS/0.1% Tween the peptides are incubated for 1 hr With FITC-labelled LPS (SIGMA; Salmonella enteriditis; 0.5 μg/ml in PBS/0.1% Tween). After washing with PBS/0.1% Tween, the ELISA plate is incubated with 100 μl of an anti-FITC antibody conjugated to alkaline phosphatase (SIGMA; 1:2500 diluted in PBS/0.1% Tween) and washed with PBS/ 0.1% Tween and 100 mM Tris pH 9.5. p-Nitrophenylphosphate (2 mg/ml in 100 mM Tris pH 9.5) is used as a substrate for alkaline phosphatase. The ELISA is read at 405 nm. All steps are done at room temperature.

Figure 12:
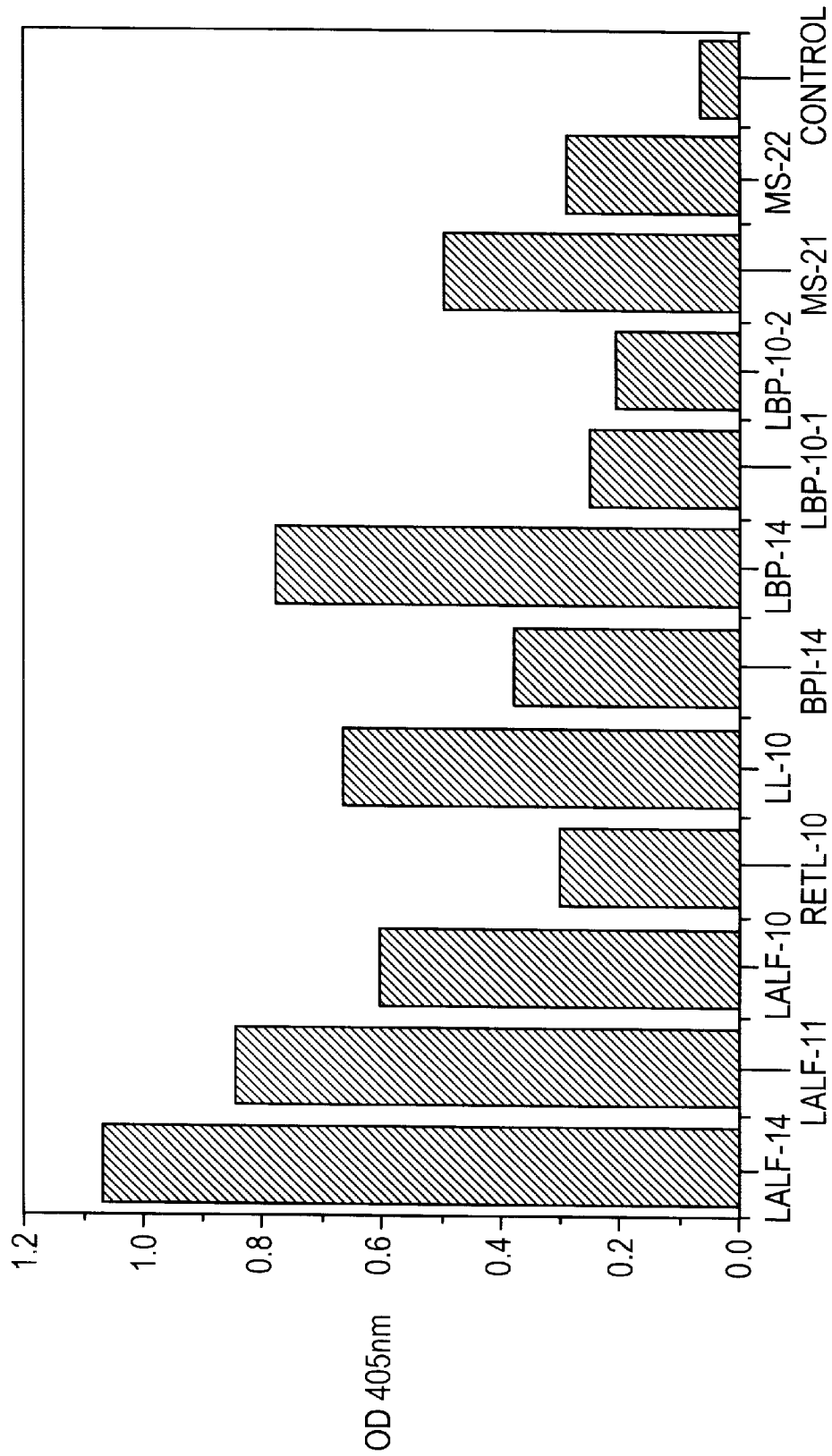
FIG. 12 shows ELISA data for the binding of fluorescein-labelled LPS to biotinylated peptides derived from LALF, LBP, BPI and the generalized motif described here, which are immobilized on the ELISA plate through interaction with streptavidin. For more details, see Example 4.

As expected, LALF-14, LALF-11, LALF-10, LBP-14 and MS-21 showed the highest binding affinity to LPS (see FIG. 12). Peptides which bind lipid A slightly above background level as determined in the alternative ELISA format, such as RETL-10, LBP-10-1 or LBP-10-2, show binding in this format clearly above (2-3 fold) background. This indicates that oligomeric binding sites for LPS can provide higher LPS binding activity.

EXAMPLE 5

Competition of LALF: lipid A Binding by Peptides

To investigate the specificity of peptides in binding lipid A and LPS, competition experiments with known endotoxin binding proteins such as LALF and LBP and the antibiotic polymyxin B are carried out. Thus an ELISA plate (NUNC, Polysorp 96U) is coated for 90 min. at 37° C. with 100 μl lipid A in PBS (0.25–0.3 μg/ml) or lipopolysaccharide in PBS (0.25–0.3 μg/ml). All further steps are done at room temperature. After washing and blocking (10 min.) with PBS/0.1% Tween, the solid phase is incubated for 1 hr with 100 μl or increasing amounts (0.01 μg/ml–100 μg/ml in PBS/0.1% Tween) of unlabelled or biotin-labelled peptides mixed with an endotoxin binding protein (LALF or LBP; 0.2 μg/ml in PBS/0.1% Tween). After washing with PBS/0.1% Tween, the ELISA plate is incubated for 45 min. with 100 μl of a rabbit antiserum against LALF or LBP, respectively. After washing with PBS/0.1% Tween the ELISA plate is incubated with 100 μl anti-rabbit antibody conjugated to alkaline phosphatase (SIGMA; 1:10000 diluted in PBS/0.1% Tween) and washed with PBS/0.1% Tween and 100 mM Tris pH 9.5. p-Nitrophenyl-phosphate (2 mg/ml in 100 mM Tris pH 9.5) is used as a substrate for alkaline phosphatase. The ELISA is read at 405 nm.

Figure 13:
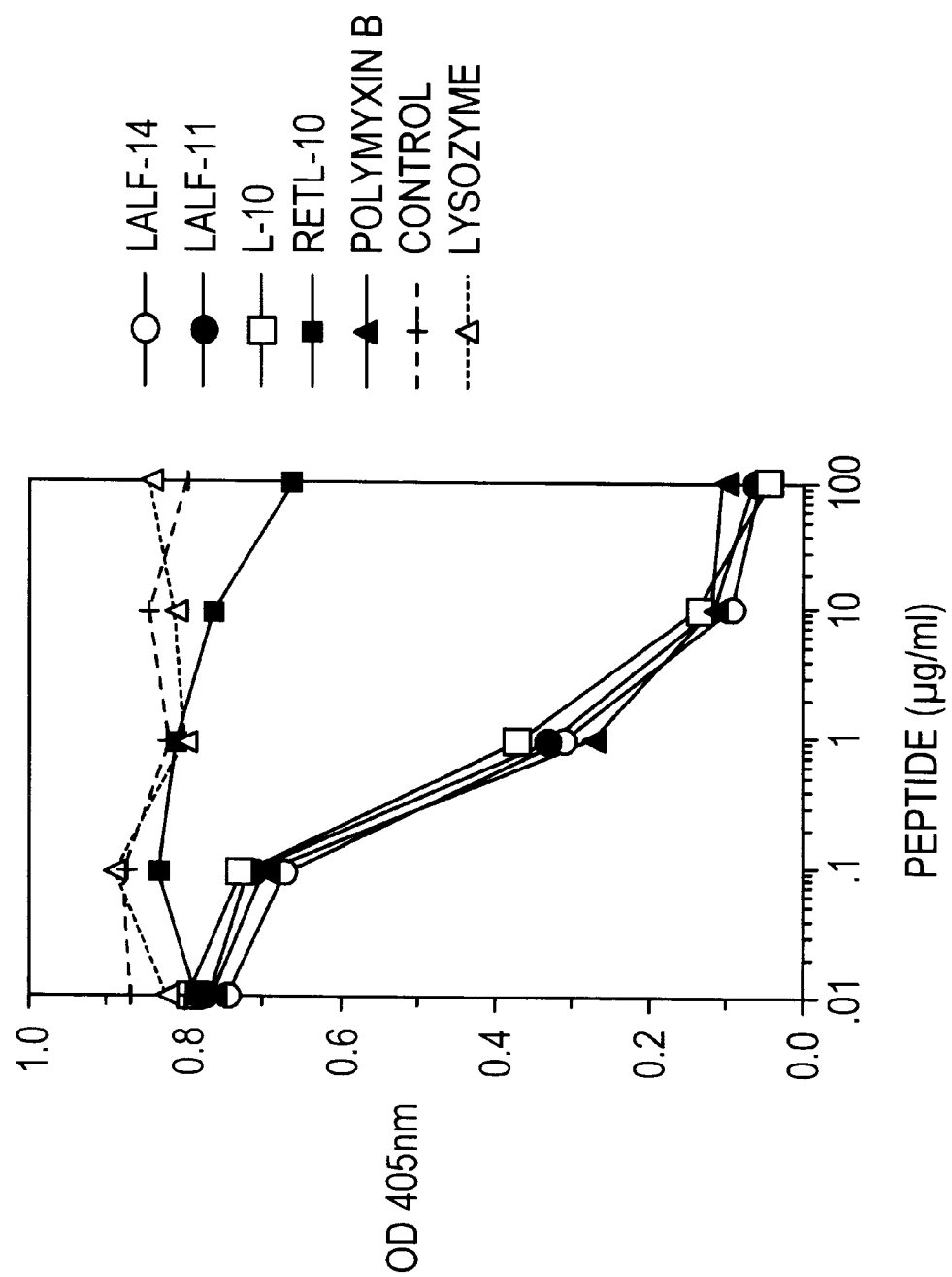
FIG. 13 shows ELISA data for the competition between LALF and LALF-derived peptides for binding to lipid A. Increasing concentrations of peptide are allowed to compete with a fixed concentration of LALF for binding to immobilized lipid A. Bound LALF is detected using an anti-rabbit antibody conjugated to alkaline phosphatase. For more details, see Example 5.

If assaying for LALF-lipid A binding, increasing amounts of peptide should lead to a decrease of detectable LALF bound to lipid A (see FIG. 13). Polymyxin B is used as a positive control, and at sufficiently high concentration is able to displace LALF almost completely from immobilized lipid A. A control peptide and lysozyme, also known to bind lipid A and LPS, are not able to compete with LALF. Of the peptides based on the LALF sequence, LALF-14, LALF-11 and L-10 are as capable as polymyxin B in competing the LALF/lipid A binding, indicating a similar LPS binding activity as polymyxin B, while RETL-10 only weakly competes with LALF.

At 100 μg/ml, LALF-14, and polymyxin B compete with LALF for lipid A binding up to 95%, while a control peptide or lysozyme compete to 10% only. Of the peptides based on LBP, H-14 competes with LALF for lipid A binding as effectively as LALF-14 or polymyxin B, while only at the highest concentrations do LBP-10-1 and H-10 inhibit the LALF lipid A binding. BPI-14 competes to a lesser extent compared with LALF-14, H-14 or polymyxin B. Of peptides based on the generalized lipid A binding motif, MS-21 competes with LALF for binding to lipid A to almost 80% while MS-22 is similar to BPI-14. PolP-1 (I-K-T-K-K-F-L-K-K-T) (SEQ ID NO:7), a peptide based on polymyxin B and shown to bind lipopolysaccharide and neutralize its toxicity (Rustici et al. *Science* 259 (1993), 361–365), hardly competes with LALF for lipid A binding.

Figure 14:
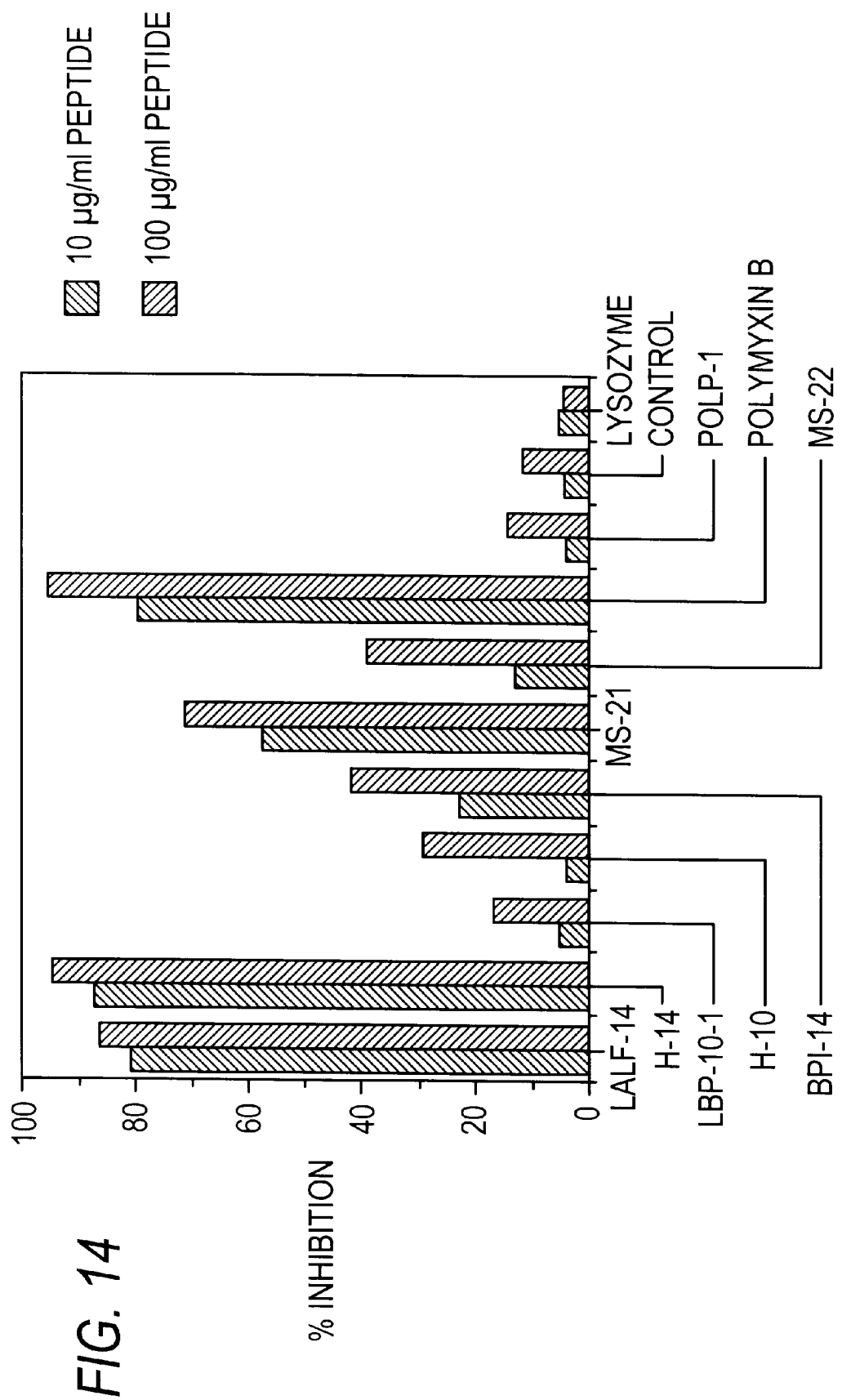
FIG. 14 shows ELISA data for the competition between LALF and various peptides for binding to immobilized lipid A at a single peptide concentration. The extent to which the peptide inhibits LALF binding (measured via an anti-rabbit antibody) to lipid A is determined at 100 µg/ml of peptide. For more details, see Example 5.

These data are presented in bar graph form in FIG. 14 for a given concentration of peptide.

EXAMPLE 6

Competition of LBP: Lipid A Binding by Peptides

Figure 15:
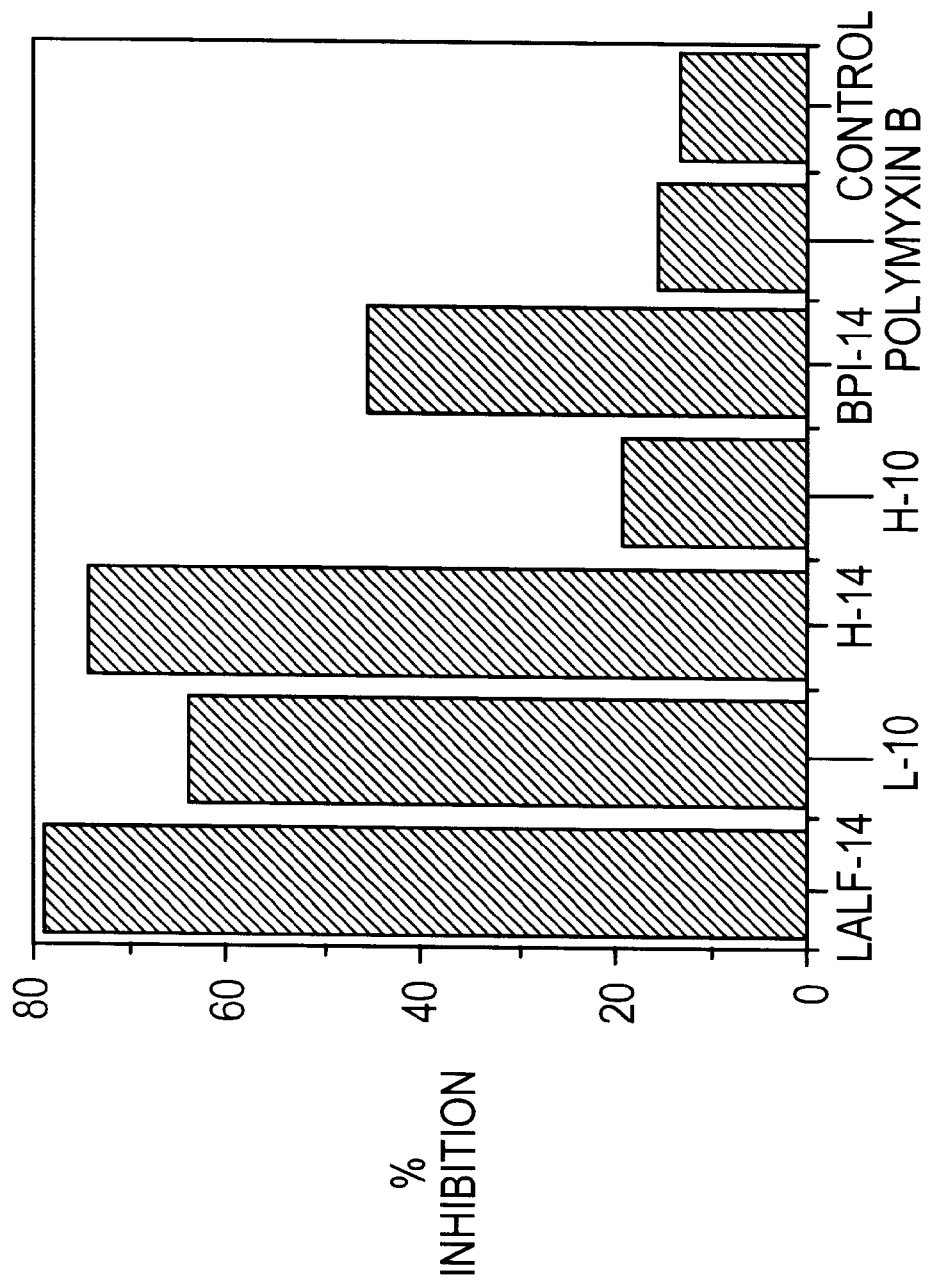
FIG. 15 shows ELISA data for the competition between LBP and various peptides for binding to immobilized lipid A at a single peptide concentration. The extent to which the peptide inhibits LBP binding (measured via an anti-rabbit antibody) to lipid A is determined at 100 µg/ml of peptide. For more details, see Example 6.

The ability of the peptides to compete with LBP for binding to LPS is determined in the same way as in Example 5, except that LALF is replaced with LBP (see FIG. 15). The result of this experiment is, with one exception, very similar to the result in FIG. 14. As shown in FIG. 15, LALF-14, L-10 and H-14 are the most potent inhibitors of the LBP-lipid A binding. In contrast to the result observed with LALF, in this case polymyxin B is not able to compete with LBP for binding to lipid A.

EXAMPLE 7

Competition of LBP14: Lipid A Binding by Peptides and Proteins

An ELISA plate (NUNC, Polysorp 96U) is coated for 90 min. at 37° C. with 100 μl lipid A in PBS (0.2–0.3 μg/ml). All further steps are done at room temperature. After washing and blocking (10 min.) with PBS/0.1%. Tween, the solid phase is incubated for 1 hr with 100 μl of increasing amounts (0.01 μg/ml–10 μg/ml) of unlabelled peptides or proteins mixed with a biotin-labelled peptide (1 μg/ml in PBST/0.1% Tween). After washing with PBS/0.1% Tween, 100μl streptavidin conjugated to alkaline phosphatase (Boehringer Mannheim GmbH, 1:10000 diluted in PBS/0.1% Tween) is added to the wells. This incubation is followed by washing with PBS/0.1% Tween and 100 mM Tris pH 9.5. p-Nitrophenyl-phosphate (2 mg/ml in 100 mM Tris pH 9.5) is used as a substrate for alkaline phosphatase. The ELISA is read at 405 nm.

Figure 16:
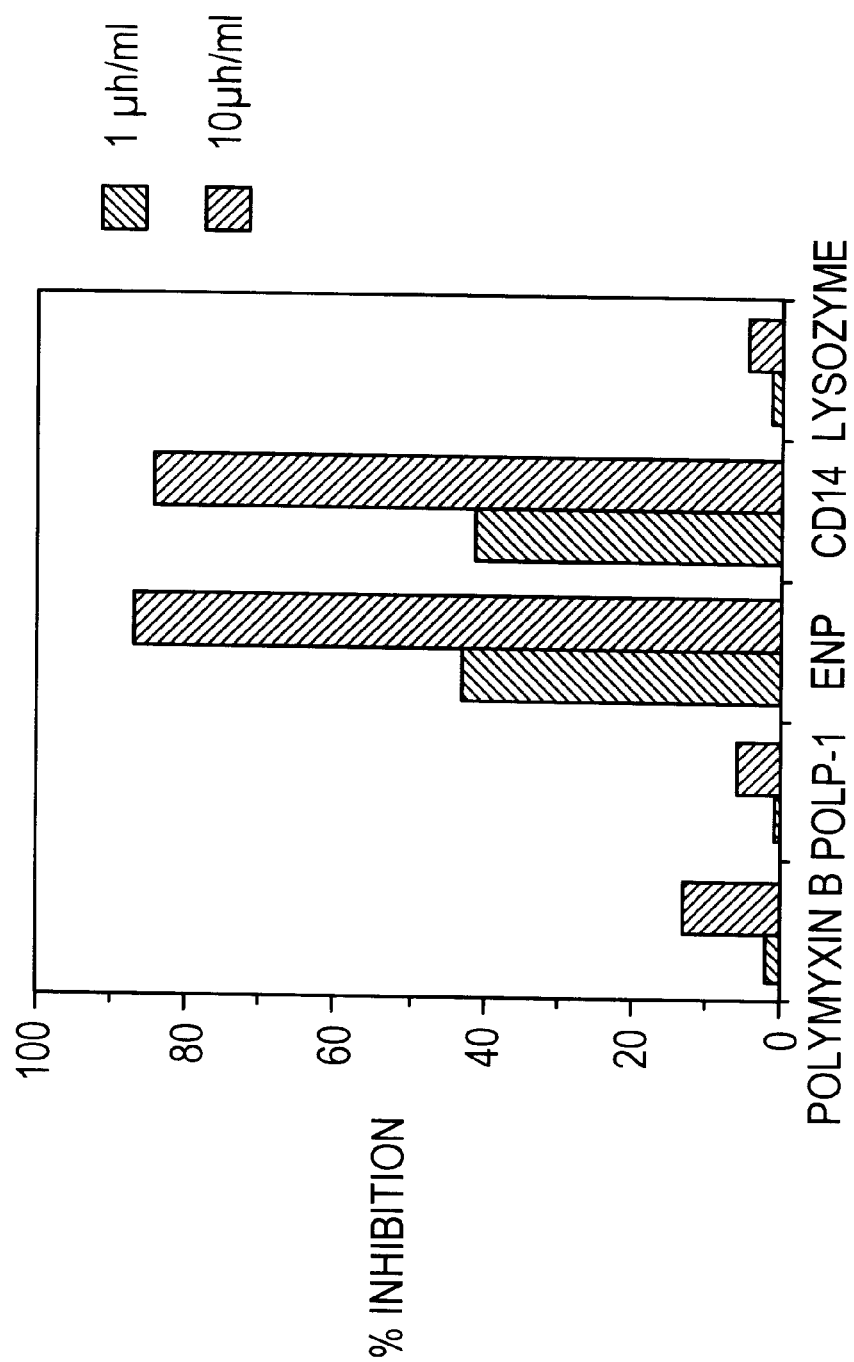
FIG. 16 shows ELISA data for the competition between the peptide LBP-14 and various peptides and proteins for binding to immobilized lipid A at a single peptide concentration. The extent to which the biotinylated LBP-14 inhibits peptide or protein binding (measured using a streptavidin-alkaline phosphatase conjugate) to lipid A is determined at 1 µg/ml and 100 µg/ml of peptide. For more details, see Example 7.

CD14 is used to compete the peptide-lipid A binding. The principle of such a binding assay is the same as for the LALF- or LBP-lipid A competition assays in which a constant amount of detectable peptide or protein is competed by an increasing amount of another peptide or protein. Instead of detecting LALF, bound biotin-labelled peptide is detected with streptavidin conjugated to alkaline phosphatase, and the labelled peptide concentration is kept constant while the unlabelled peptide or protein amount is increased. The binding of LBP-14 to lipid A binding is strongly competed by LALF and CD14, while polymyxin B shows only weak competition activity at the highest concentration used (see FIG. 16). PolP-1 is only slightly above the background determined by lysozyme as competitor. A very similar result is observed when LALF-14 is used instead of LBP-14. These results indicate that the peptides LBP-14 and LALF-14 are able to compete with CD14 for lipid A binding.

EXAMPLE 8

Influence of Serum on Peptide-lipid A Binding

Figure 17:
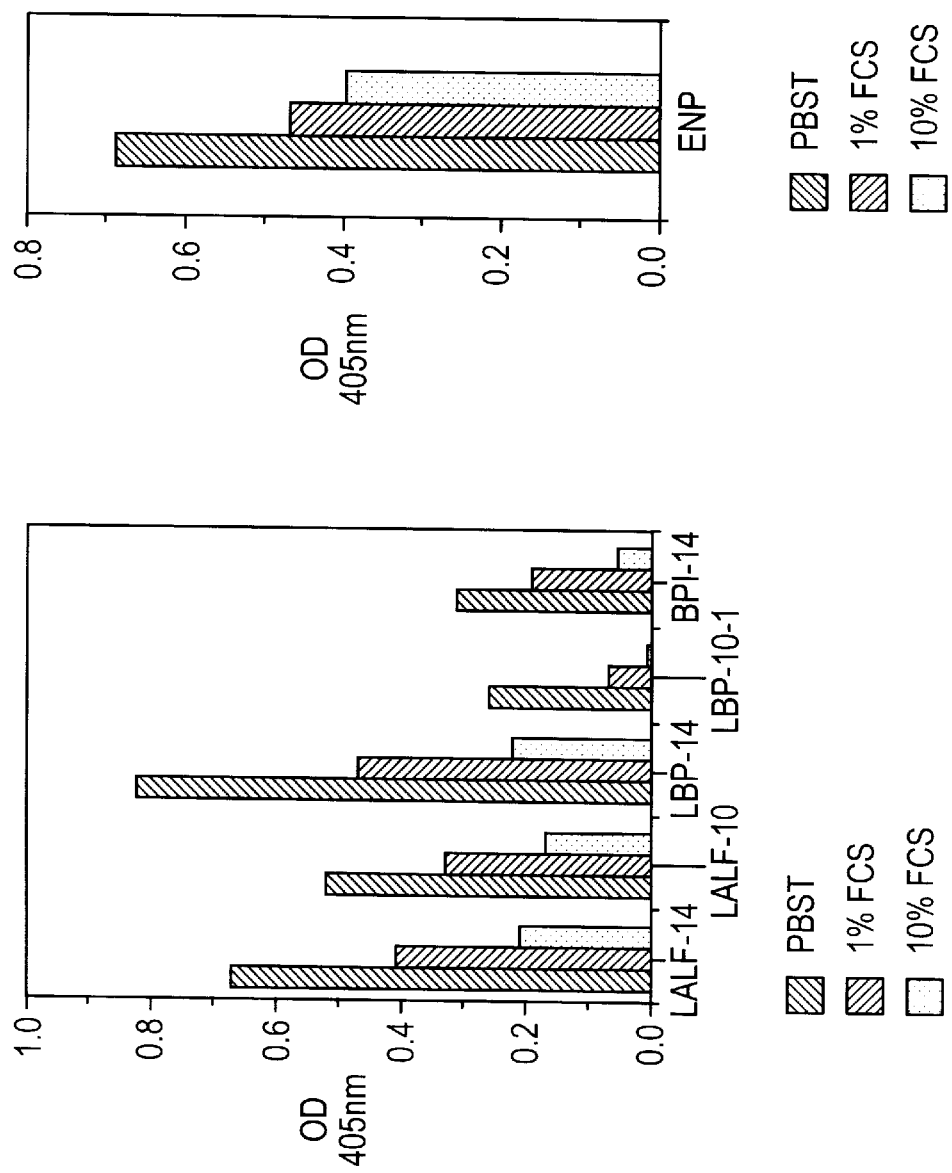
FIGS. 17A and B shows ELISA data which illustrates the effect of increasing concentrations of serum on the binding of peptides to immobilized lipid A. Biotinylated peptides are detected using a streptavidin-alkaline phosphatase conjugate. For more details, see Example 8.

To determine the effect of serum proteins on peptide-lipid A binding, the interaction of labelled peptides is measured in an ELISA format in the presence of serum concentrations of 1% and 10% and compared with binding in buffer or medium. For all peptides tested, LALF-14, LALF-10, LBP-14, LBP-10-1 and BPI-14, the lipid A binding activity decreases with increasing serum concentration, but the peptides are still able to bind lipid A at 10% serum (see FIG. 17). As control, the influence of serum on the LALF-lipid A binding was investigated, and a serum-dependent decrease of the LALF-lipid A binding is observed.

EXAMPLE 9

Influence of Serum on the Competition of the LALF: Lipid A Binding by Peptide

Figure 18:
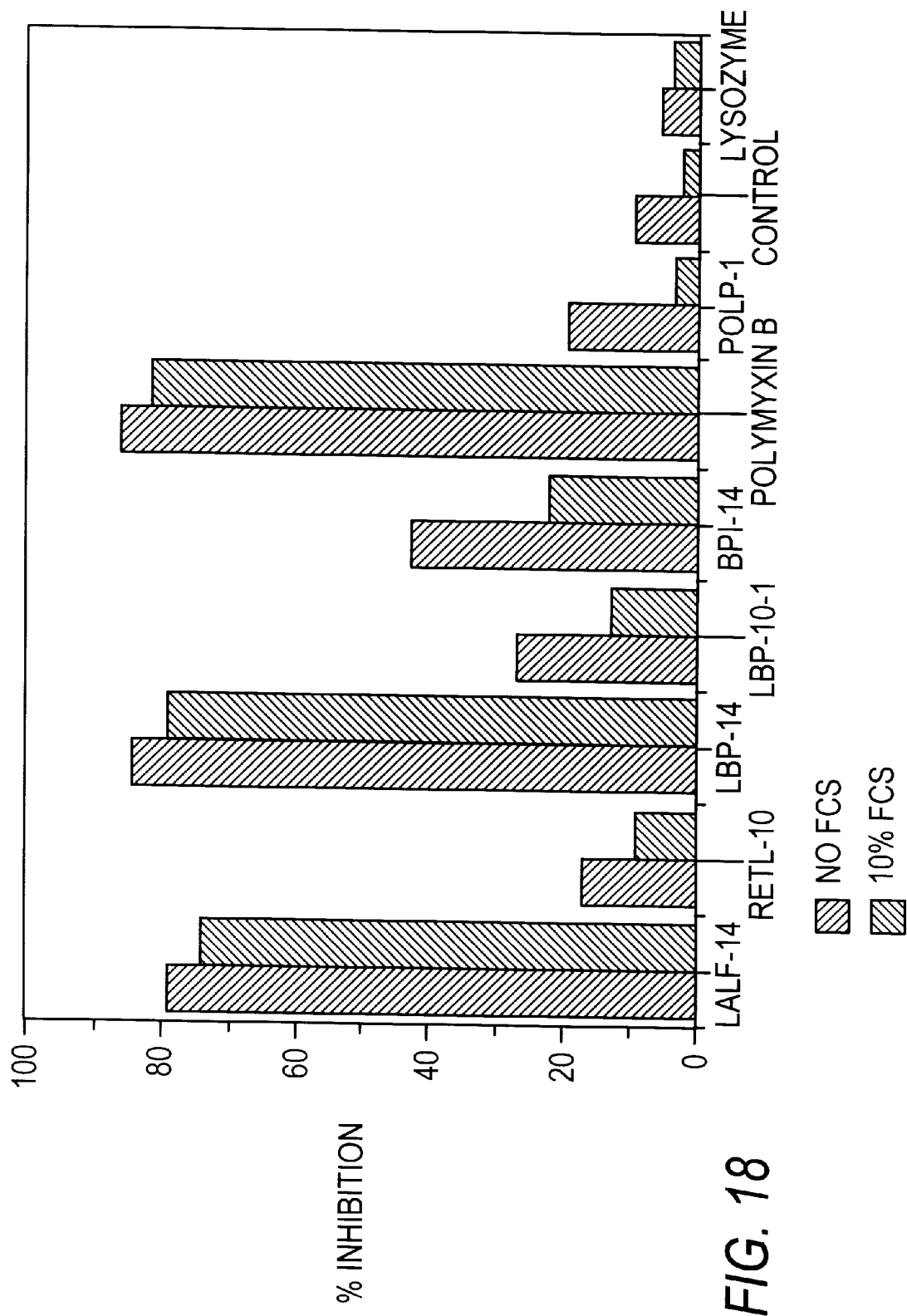
FIG. 18 shows ELISA data which illustrates the effect of increasing concentrations of serum on the ability of peptides to compete with LALF for binding to immobilized lipid A. The extent to which the peptide inhibits LALF binding (measured via an anti-rabbit antibody) to lipid A is determined at 100 µg/ml of peptide of 0% and 10% fetal calf serum. For more details, see Example 9.

To investigate whether the specificity of the peptide-lipid A binding is influenced by serum, competition experiments are performed in which LALF-lipid A binding is compared in PBS/0.1% Tween and serum. In all cases only a slight decrease (ca. 5%) of the competition capacity of the peptides in the presence of 10% serum is observed compared to 0% serum (see FIG. 18). However the peptides that compete efficiently with LALF for lipid A binding in buffer, such as LALF-14, LBP-14 and polymyxin B, which was used as a control, are also inhibiting in the presence of 10% serum. BPI-14 competes with LALF for lipid A binding to a lesser extent in the presence of 10% serum, and RETL-10 or the polymyxin derived peptide Pol P1 only inhibit slightly above background.

EXAMPLE 10

Limulus Amebocyte Lysate Assay

Figure 19:
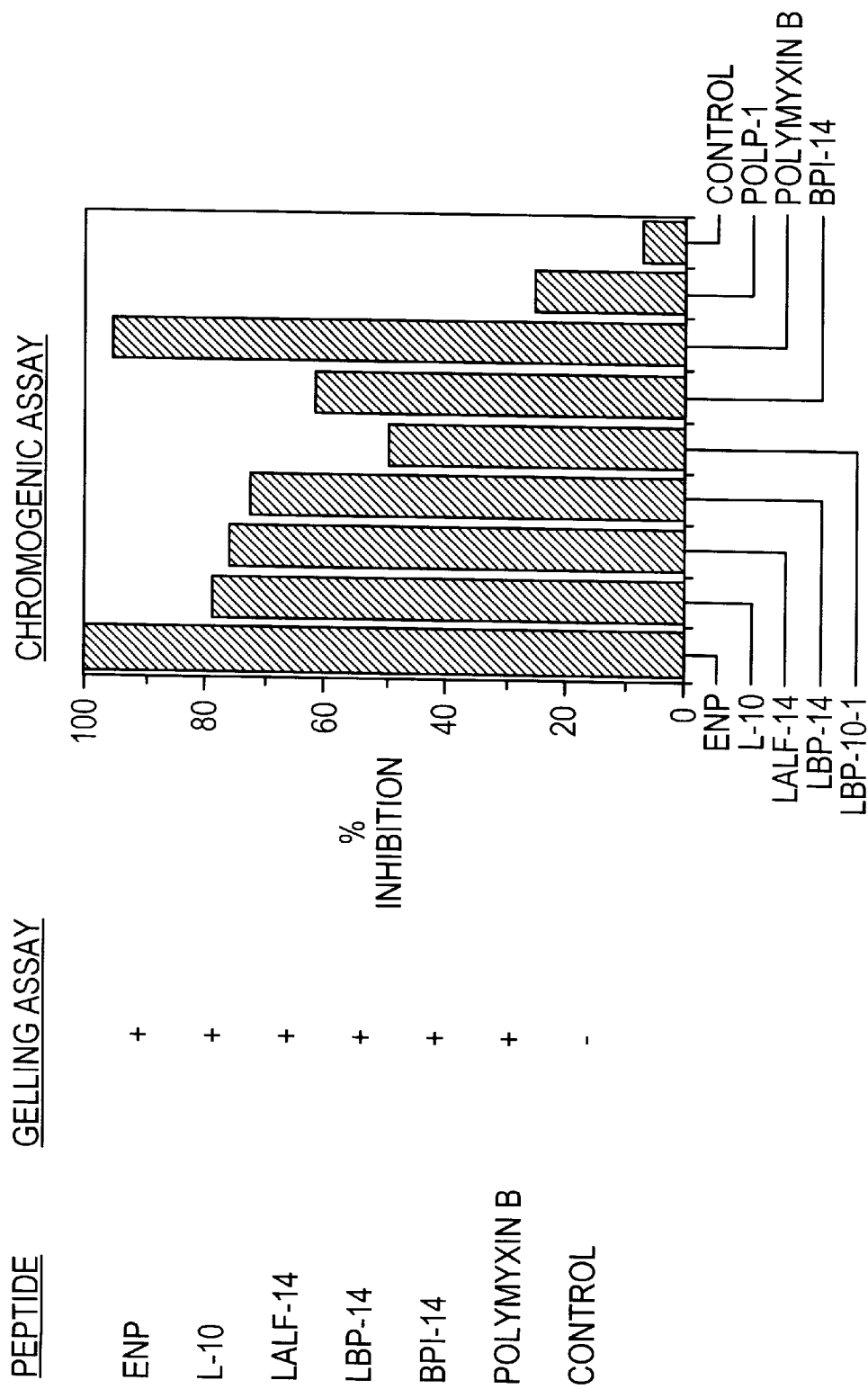
FIG. 19 shows data for the inhibition by peptides of the Limulus amebocyte lysate gelling and chromogenic assays. The peptides are tested either for their ability to inhibit LPS-mediated gelling of Limulus amebocyte lysates or to inhibit the LPS-colour reaction in the chromogenic Limulus amebocyte lysate assay. For more details, see Example 10.

The Limulus amebocyte Lysate test (gelling assay; sensitivity 0.125 EU/ml) and the Chromogenic Limulus amebocyte Lysate test (sensitivity 0.06 EU/ml) are performed according to the manufacturer's instruction (Bio*Whittaker, Walkersville, Md.) using *E. coli* 055:B5 lipopolysaccharide. For neutralisation of LPS, peptides (0.1–10 μg/ml) and LPS are incubated for 15 min. at 37° C. and then added to the Limulus lysate. In the gelling assay, the positive controls, LALF and polymyxin B, inhibit the assays, the control peptide (control) does not (see FIG. 19). L-10, LALF-14, LBP-14, and BPI-14 are also able to inhibit the lysate assay, indicating neutralizing activity (FIG. 19). The chromogenic assay allows quantification of the lipopolysaccharide neutralizing capacity of the peptides. LALF and polymyxin B inhibit the reaction up to 95%. Of the peptides, L-10, LALF-14, and LBP14 are best inhibiting (up to 79%). BPI-14 inhibits the chromogenic assay up to 63%, LBP-10-1, a weak competitor of LALF- and LBP-lipid A binding, inhibits the assay up to 50%, while Pol P1, known to inhibit the gelling assay, inhibits the chromogenic assay only up to 25%.

EXAMPLE 11

Inhibition by Peptides of LPS-mediated TNF Release by Monocytes

Monocytes are purified with a ficoll gradient (d=1.077) from whole blood by centrifugation for 20 min. at 2200 rpm at room temperature. Ficoll is removed by washing 3 times with PBS. Purified monocytes are counted and diluted to $2 \times 10^6$ cells/900 μl in medium (RPMI+) or medium with 0.1%–10% human serum. For TNF induction, $2 \times 10^6$ monocytes (in 900 μl medium or medium with serum) and 100 μl of LPS (Re-LPS F515; 0.1 ng/ml–10 ng/ml) or mixtures of LPS with peptides (10 μg/ml) (preincubated for 15 min. at 37° C.) are incubated in a 24 well plate (NUNC) for 2 to 5 hr. The supernatant is taken off and spun twice for 2 min. at 1500 rpm, once for 5 min. at 15000 rpm and stored at −20° C. for TNF determination. The induced TNF is assayed by ELISA according to the manufacturer's instruction (BioSource International, California) using a 50 μl sample of thawed supernatant.

Figure 20:
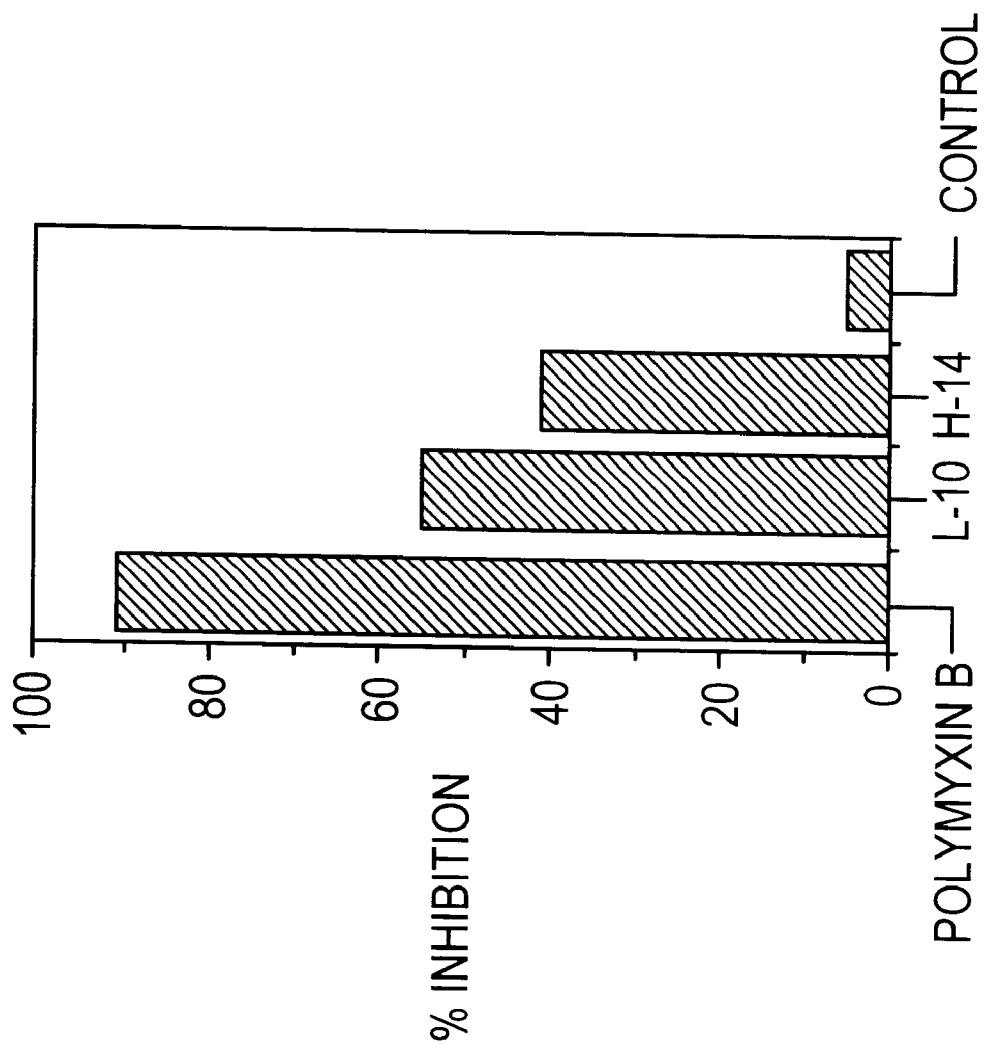
FIG. 20 shows data or the inhibition, by a fixed concentration of four different peptides, of the LPS-mediated release of tumour necrosis factor by monocytes. TNF is detected using a commercial ELISA kit. For more details, see Example 11.

L-10 and LBP-14 show 55% inhibition of TNF release, under the same conditions as polymyxin B shows 95% inhibition of TNF release (see FIG. 20).

---

What is claimed is:

1. An apparatus for the removal of LPS from a solution, said apparatus comprising an LPS-binding peptide immobilized on a solid support, wherein the LPS-binding peptide is capable of interacting with LPS with an association constant greater than $10^5$ $M^{-1}$, and consists of 22 or less amino acids which comprises at least:

(a) the amino acid sequence 1-2-3-4-5-6-7-8, wherein the numbers represent any of the following amino acids:
        1=C, H, K, N, Q, R, S, T, W, or Y;
        2=A, F, H, I, L, M, V, or W;
        3=H, K, or R;
        4=A, F, H, I, K, L, M, R, V, or W;
        5=A, C, F, H, I, K, L, M, N, Q, R, S, T, V, W, or Y;
        6=K or R;
        7=C, F, H, I, K, L, M, N, Q, R, S, T, V, W, or Y;
        8=A, F, H, I, K, L, M, R, V, or W;

(b) a corresponding inverse amino acid sequence.

2. The apparatus according to claim 1 comprising the amino acid sequence 1-2-3-4-5-6-7-8, wherein the numbers represent any of the following amino acids:

1=T or R or K
    2=F or W
    3=R or K
    4=R or V or A
    5=L or R or Q
    6=K
    7=W or S or R
    8=K or F.

3. The apparatus according to claim 1 or 2, wherein the N-terminus of the LPS-binding domain is extended by two or more amino acids denoted −2 and −1 in which amino acid −2, which is the new N-terminus, is taken from the set R, K, H, N and Q, and amino acid −1 is any amino acid.

4. The apparatus according to claim 3, wherein the C-terminus of the LPS-binding domain is extended by addition of cysteine, and the N-terminus is extended by two or more amino acids denoted −2 and −1 in which amino acid −2, which is the new N-terminus, is taken from the set R, K, H, N and Q, and amino acid −1 is cysteine, the two cysteines being linked by a disulfide bond.

5. The apparatus according to claim 1 or 2, wherein the C-terminus of the LPS-binding domain is extended by addition of cysteine, and the N-terminus is extended by two or more amino acids denoted −2 and −1 in which amino acid −2, which is the new N-terminus, is taken from the set R, K, H, N and Q, and amino acid −1 is cysteine, the two cysteines being linked by a disulfide bond.

6. The apparatus according to claim 1 or 2, wherein said amino acid sequence (a) is the sequence TFRRLKWK(SEQ ID NO:1).

7. The apparatus according to claim 1 or 2, wherein said amino acid sequence (a) is the sequence RWKVRKSFFKLQ.

8. The apparatus according to claim 1 or 2, wherein said amino acid sequence (a) is the sequence KWKAQKRFLKMS.

9. The apparatus according to claim 1 or 2, wherein the LPS-binding peptide is a linear peptide.

10. The apparatus according to claim 1 or 2, wherein the LPS-binding peptide is constrained to adopt a circular conformation by an intramolecular interaction.

11. The apparatus according to claim 10, wherein said interaction is a disulfide bond.

12. The apparatus according to claim 11, wherein the LPS-binding peptide has the amino acid sequence CHYRIKPTFRRLKWKYKGKFWC, CTFRRLKWKC, CRWKVRKSFFKLQC, CRWKVRKSFC, CKWKAQKRFLKMSC, or CKWKAQKRFC and the peptide is stabilized by a disulfide bond formed between the terminal cysteine residues.

13. A method of removing LPS from a solution using the apparatus of any one of claims 1, 2, 4, 11, or 12.

14. The method according to claim 13 wherein said apparatus is used for the removal of bacteria from a solution.

15. The apparatus according to claim 1 or 2, wherein the LPS-binding peptide is detectably labelled.

16. An apparatus for the removal of LPS from a solution, said apparatus comprising an LPS-binding peptide comprising an LPS-binding domain of 22 or less amino acids which comprises at least:

(a) the amino acid sequence 1-2-3-4-5-6-7-8, wherein the numbers represent any of the following amino acids:
        1=C, H, K, N, Q, R, S, T, W, or Y;
        2=A, F, H, I, L, M, V, or W;
        3=H, K, or R;
        4=A, F, H, I, K, L, M, R, V, or W;
        5=A, C, F, H, I, K, L, M, N, Q, R, S, T, V, W, or Y;
        6=K or R;

7=C, F, H, I, K, L, M, N, Q, R, S, T, V, W, or Y;
8=A, F, H, I, K, L, M, R, V, or W; or (b) corresponding inverse amino acid sequence; with the proviso that said LPS-binding domain is not contiguous with sequences outside the LPS-binding domains of any of the following:

i) polymyxins;
ii) lipopolysaccharide binding protein;
iii) Limulus anti-LPS factor; or
iv) bactericidal/permeability-increasing protein.

* * * * *